US011160447B2

(12) United States Patent
Hetling et al.

(10) Patent No.: US 11,160,447 B2
(45) Date of Patent: Nov. 2, 2021

(54) PIXELATED, FULL-FIELD MULTI-PROTOCOL STIMULUS SOURCE APPARATUS, METHOD AND SYSTEM FOR PROBING VISUAL PATHWAY FUNCTION

(71) Applicant: The Board of Trustees of The University Of Illinois, Urbana, IL (US)

(72) Inventors: John R. Hetling, Dyer, IN (US); Shresta Patangay, Chicago, IL (US); Meagan Ouy, Skokie, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 734 days.

(21) Appl. No.: 15/753,305

(22) PCT Filed: Aug. 23, 2016

(86) PCT No.: PCT/US2016/048129
§ 371 (c)(1),
(2) Date: Feb. 17, 2018

(87) PCT Pub. No.: WO2017/035113
PCT Pub. Date: Mar. 2, 2017

(65) Prior Publication Data
US 2018/0242834 A1    Aug. 30, 2018

Related U.S. Application Data

(60) Provisional application No. 62/209,123, filed on Aug. 24, 2015.

(51) Int. Cl.
*A61B 3/00* (2006.01)
*A61B 3/024* (2006.01)
(Continued)

(52) U.S. Cl.
CPC ............ *A61B 3/0008* (2013.01); *A61B 3/005* (2013.01); *A61B 3/0091* (2013.01); *A61B 3/022* (2013.01);
(Continued)

(58) Field of Classification Search
CPC ....... A61B 3/0008; A61B 3/005; A61B 3/022; A61B 5/04842; A61B 3/024; A61B 3/0091
See application file for complete search history.

(56) References Cited

U.S. PATENT DOCUMENTS 3,421,498 A    1/1969   Gans
4,063,807 A *  12/1977  Gelius ................... A61B 3/024
                                              351/226
(Continued)

FOREIGN PATENT DOCUMENTS

DE              2507723 A1    8/1976
GB               694128 A     7/1953
WO        WO-2014/172625 A1  10/2014

OTHER PUBLICATIONS

Supplementary European Search Report issued in European Patent Application No. 16839967 dated Apr. 18, 2019.

*Primary Examiner* — Sean P Dougherty
(74) *Attorney, Agent, or Firm* — Marshall, Gerstein & Borun LLP

(57) ABSTRACT

A pixel light source apparatus, system and method are disclosed for a stimulus source for visual pathway testing. A representative system includes a plurality of pixel light sources and a control and driver circuit. The pixel light sources are coupled to each other to form a partially-spherical dome, with each pixel light source arranged to emit light directed to a convergent location of the partially-spherical dome. The control and driver circuit implements a selected stimulus protocol to selectively energize each pixel (Continued)

light source to generate light stimulation to any arbitrary or selected portion of the retina of an eye of a human subject. A representative pixel light source comprises at least one elongated and optically opaque side wall; a rear wall; an illumination source; a first optical element defining a first light chamber; and a second optical element defining a second light chamber.

33 Claims, 19 Drawing Sheets

(51) Int. Cl.
    *A61B 5/378*     (2021.01)
    *A61B 5/398*     (2021.01)
    *A61B 3/02*     (2006.01)
    *A61B 5/16*     (2006.01)
    *A61B 5/00*     (2006.01)

(52) U.S. Cl.
    CPC ............. *A61B 3/024* (2013.01); *A61B 5/161* (2013.01); *A61B 5/378* (2021.01); *A61B 5/398* (2021.01); *A61B 5/4848* (2013.01); *A61B 5/7246* (2013.01)

(56) References Cited

U.S. PATENT DOCUMENTS

| | | | | |
|---|---|---|---|---|
| 4,750,831 | A * | 6/1988 | Vega | A61B 3/107 351/223 |
| 4,844,607 | A * | 7/1989 | Andera | A61B 3/022 351/243 |
| 5,024,519 | A * | 6/1991 | Howard | A61B 3/024 351/224 |
| 5,694,199 | A * | 12/1997 | Rodriguez | A61B 3/022 351/223 |
| 5,835,188 | A * | 11/1998 | Moreno | A61H 5/00 351/203 |
| 6,144,508 | A * | 11/2000 | Bransome | A61B 3/0008 351/223 |
| 8,079,706 | B2 * | 12/2011 | Silvestrini | A61B 3/0091 351/200 |
| 10,667,683 | B2 * | 6/2020 | Jackson | A61B 3/028 |
| 2003/0088169 | A1 * | 5/2003 | Percival | A61B 3/0091 600/399 |
| 2003/0147499 | A1 * | 8/2003 | Kondo | G03F 7/70575 378/119 |
| 2006/0087618 | A1 * | 4/2006 | Smart | A61H 5/005 351/222 |
| 2006/0238704 | A1 * | 10/2006 | Donnerhacke | A61B 3/112 351/200 |
| 2007/0235639 | A1 * | 10/2007 | Rains, Jr. | F21V 7/30 250/228 |
| 2007/0242222 | A1 * | 10/2007 | Iwanaga | A61B 3/0091 351/211 |
| 2007/0242223 | A1 * | 10/2007 | Nakagawa | A61B 3/0008 351/221 |
| 2010/0271840 | A1 * | 10/2010 | Hamada | G02F 1/133606 362/606 |
| 2011/0043756 | A1 * | 2/2011 | Kahn | G01J 3/32 351/206 |
| 2011/0279007 | A1 * | 11/2011 | Kishimoto | F21S 41/13 313/45 |
| 2012/0212598 | A1 * | 8/2012 | Mowrey | A61B 5/0013 348/78 |
| 2014/0078467 | A1 * | 3/2014 | Su | A61B 3/132 351/207 |
| 2014/0132932 | A1 * | 5/2014 | Jung | A61B 3/0008 351/221 |
| 2014/0355101 | A1 * | 12/2014 | Shian | G02B 26/005 359/290 |
| 2015/0009473 | A1 * | 1/2015 | Su | A61B 3/145 351/206 |
| 2015/0078705 | A1 * | 3/2015 | Wang | G02B 6/4204 385/33 |
| 2015/0138505 | A1 * | 5/2015 | Grenon | A61B 3/0008 351/206 |
| 2015/0208911 | A1 * | 7/2015 | Funamoto | A61B 3/12 351/221 |
| 2015/0230703 | A1 * | 8/2015 | Wharton | A61B 3/0008 351/221 |
| 2015/0313467 | A1 * | 11/2015 | Sakai | A61B 3/0016 351/208 |
| 2016/0128569 | A1 * | 5/2016 | Cheng | A61B 3/14 351/206 |
| 2016/0228001 | A1 * | 8/2016 | Choate | A61B 3/0008 |
| 2016/0262611 | A1 * | 9/2016 | Rotenstreich | A61B 3/0041 |
| 2016/0287070 | A1 * | 10/2016 | Wang | A61B 3/0075 |
| 2017/0000338 | A1 * | 1/2017 | Davis | A61B 3/0025 |
| 2017/0065167 | A1 * | 3/2017 | Walmsley | A61B 3/0008 |

* cited by examiner

# PIXELATED, FULL-FIELD MULTI-PROTOCOL STIMULUS SOURCE APPARATUS, METHOD AND SYSTEM FOR PROBING VISUAL PATHWAY FUNCTION

CROSS-REFERENCE TO RELATED APPLICATIONS

This application is a U.S. national phase under 35 U.S.C. Section 371 and claims the benefit of and priority to International Application No. PCT/US2016/048129 filed Aug. 23, 2016, which is a nonprovisional of and claims the benefit of and priority to U.S. Provisional Patent Application No. 62/209,123, filed Aug. 24, 2015, inventors John R. Hetling et al., titled "Pixelated Full-Field Electroretinogram Stimulus Source for Probing Local Retinal Function", which is commonly assigned herewith, and all of which is hereby incorporated herein by reference in its entirety with the same full force and effect as if set forth in its entirety herein.

FIELD OF THE INVENTION

The present invention, in general, relates to visual stimulation sources utilized in electroretinography, visual-evoked potential testing, and other visual pathway testing protocols, and more particularly, relates to an apparatus, method and system for a pixelated, full-field multi-protocol stimulus source for probing visual pathway function, such for electroretinography protocols, visual-evoked potential protocols, psychophysical testing protocols, and other visual pathway testing protocols.

BACKGROUND OF THE INVENTION

Most retinal diseases begin in one part of the retina and spread to other areas. For example, many retinal diseases such as glaucoma may begin in a peripheral part of the retina, before spreading to the more central regions of the retina. To detect such diseases early in their onset, a sensitive measure of local retinal health is required. Existing detection methods, however, are largely limited to examination of the central retina. The electroretinogram (or, equivalently, electroretinography) ("ERG") is one popular test used to determine the health of the retina. Currently available ERG stimulus sources, however, cannot stimulate or address any arbitrary or selected area of the entire retina. As a result, a local area of dysfunction in the retina often cannot be detected, particularly when the electroretinography signal may be dominated by signals from the rest of the retina, which may be healthy and functioning properly.

For ERG, many current systems use flat computer monitors as stimulation sources to test the retina. Such flat monitors, however, are incapable of generating stimuli which fill the entire visual field, even if the monitor were very large and positioned impractically close to the subject being tested.

Existing three-dimensional ERG stimulus sources are uniformly luminous, and merely reflect light evenly from an entire concave surface. The only focal ERG stimulus sources are limited to the central visual field, and are technically difficult to implement and/or produce results that can be difficult to interpret.

For example, while the current Goldmann perimetry test identifies the outer limits of the visual field, it is a difficult test to administer, requiring a skilled technician, is considered somewhat subjective, and has poor reproducibility.

Accordingly, a need remains for a stimulus source which can provide selective and precise stimulation to any part of a retina, including both central and peripheral retina. Such a stimulation source should also be capable of generating any stimulus pattern for any type of ERG, visual-evoked potential ("VEP") and/or psychophysical testing for the retina, the optic nerve, and the visual cortex, and further should avoid erroneous or unwanted stimulation or stimulation reflections of retinal or other areas which could interfere with the selected testing. Such a stimulus source should also be able to identify the limits of the visual field in an objective manner, without requiring a skilled technician.

BRIEF SUMMARY OF THE INVENTION

The representative embodiments of the present invention provide numerous advantages. The representative apparatus, system and method embodiments provide for a stimulus source which can provide selective and precise stimulation to any part of a retina, including both central and peripheral retina. The representative apparatus, system and method embodiments are also capable of generating any stimulus pattern for any type of ERG, VEP and/or psychophysical testing for the retina, the optic nerve, and the visual cortex, and further avoid erroneous or unwanted stimulation or stimulation reflections of retinal or other areas which could interfere with the selected testing. The representative apparatus, system and method embodiments also provide an ERG, VEP and/or psychophysical testing stimulus source which is able to identify the limits of the visual field in an objective manner, without requiring a skilled technician.

A representative pixel light source apparatus embodiment for a stimulus source for visual pathway testing is disclosed, with the representative pixel light source apparatus embodiment comprising: at least one side wall, the at least one side wall elongated in a longitudinal dimension and optically opaque; a rear wall coupled to the at least one side wall, the rear wall forming a distal end; an illumination source arranged at or adjacent the distal end; a first optical element coupled to the at least one side wall and spaced apart proximally from the illumination source to define a first light chamber; and a second optical element coupled to the at least one side wall and spaced apart proximally from the first optical element to define a second light chamber.

In a representative embodiment, the second optical element is optically transmissive, with the second optical element having a first surface on a first side facing the second light chamber and having a second surface opposite the first surface and forming a proximal end, wherein the second optical element further comprises an anti-reflective coating on the second surface.

In a representative embodiment, the second optical element is optically transmissive, with the second optical element having a first surface on a first side facing the second light chamber and having a second surface opposite the first surface and forming a proximal end, wherein the second optical element further comprises a first anti-reflective coating on the first surface and a second anti-reflective coating on the second surface.

In a representative embodiment, the illumination source comprises one or more light emitting diodes. For example, the one or more light emitting diodes may further comprise: at least one first light emitting diode for emission of red light or for light emission in a first spectral range; at least one second light emitting diode for emission of green light or for light emission in a second spectral range; at least one third light emitting diode for emission of blue light or for light emission in a third spectral range; and at least one fourth light emitting diode for emission of white light or for light emission in a fourth spectral range.

In a representative embodiment, each of the first optical element and the second optical element may be a translucent diffusing optical element.

In a representative embodiment, the pixel light source apparatus may further comprise: a reflective coating covering at least part of the rear wall and at least part of the at least one side wall within the first light chamber. For example, the reflective coating may be selected from the group consisting of: barium sulfate, a white paint, a silver paint, a white polymer, a reflective polymer, a nano-structured reflective composition, zinc sulfide, titanium dioxide, magnesium fluoride, silicon dioxide, and combinations thereof.

In a representative embodiment, the pixel light source apparatus may further comprise: a non-reflective coating covering at least part of the at least one side wall within the second light chamber. For example, the non-reflective coating may be selected from the group consisting of: a flat black paint, a flocking, carbon black, carbon nanotubes, a nano-structured light absorbing composition, and combinations thereof.

In a representative embodiment, the pixel light source apparatus may further comprise: a transparent or translucent lens or cover coupled to the illumination source. In another representative embodiment, the pixel light source apparatus may further comprise: a third optical element coupled to the at least one side wall, the third optical element arranged between and spaced-apart from the illumination source and the first optical element.

In a representative embodiment, the at least one side wall may further comprise: a plurality of side walls coupled to each other to form an elongated polygonal structure enclosing the first and second light chambers in a transverse dimension. For example, the elongated polygonal structure, together with the rear wall and the second optical element, may define a frustum selected from the group consisting of: a pyramidal frustum, a triangular frustum, a square frustum, a pentagonal frustum, a hexagonal frustum, a septagonal frustum, an octagonal frustum, a conical frustum, and combinations thereof.

In a representative embodiment, a plurality of pixel light source apparatuses are coupled to each other to form a partially-spherical dome or shell.

A representative pixel light source system embodiment for a stimulus source for visual pathway testing is disclosed, with the representative pixel light source system embodiment comprising: a plurality of pixel light sources coupled to each other to form a partially-spherical dome, each pixel light source arranged to emit light directed to a convergent location of the partially-spherical dome; and a control and driver circuit coupled to the plurality of pixel light sources, the control and driver circuit adapted to implement a selected stimulus protocol to selectively energize each pixel light source of the plurality of pixel light sources.

In a representative embodiment, the control and driver circuit may comprise: a memory storing the selected stimulus protocol and a plurality of instructions; a plurality of switches, each switch coupled to a corresponding pixel light source of the plurality of pixel light sources; one or more current regulation circuits coupled to the plurality of switches; and a controller coupled to the plurality of switches and the one or more current regulation circuits, the controller adapted to generate a plurality of signals to the plurality of switches and the one or more current regulation circuits to selectively energize and de-energize each pixel light source of the plurality of pixel light sources according to the selected stimulus protocol and in response to the plurality of instructions.

In a representative embodiment, the controller may be further adapted to generate a plurality of signals to the plurality of switches and the one or more current regulation circuits to select a subset of the plurality of pixel light sources and to selectively energize and de-energize each pixel light source of the subset of the plurality of pixel light sources at a corresponding selected intensity, a corresponding selected spectral range, and a corresponding selected temporal frequency.

For example, the selected stimulus protocol is an electroretinogram (ERG) protocol, or a Visual-Evoked Potential (VEP) protocol, or a Psychophysical Test protocol, may be selected from the group consisting of: a patterned stimulus protocol, a focal ERG or VEP stimulus protocol, a multi-focal ERG or VEP stimulus protocol, a pseudo-random pattern protocol, a chromatic focal ERG or VEP protocol, a pattern ERG or VEP protocol, a full-field (Ganzfeld) stimulus protocol, a flash ERG or VEP protocol, a paired-flash ERG or VEP protocol, a flicker ERG or VEP protocol, a scotopic threshold response (STR) protocol, a photopic negative response (PhNR) protocol, a step response protocol, an ON response protocol, an OFF response protocol, a chromatic response protocol, a visual field/perimetry protocol, a contrast sensitivity protocol, and combinations thereof.

In a representative system embodiment, each pixel light source is an apparatus comprising: at least one side wall, the at least one side wall elongated in a longitudinal dimension and optically opaque; a rear wall coupled to the at least one side wall, the rear wall forming a distal end; an illumination source arranged at or adjacent the distal end, the illumination source comprising one or more light emitting diodes; a first, diffusing optical element coupled to the at least one side wall and spaced apart proximally from the illumination source to define a first light chamber; and a second, optically transmissive optical element coupled to the at least one side wall and spaced apart proximally from the first optical element to define a second light chamber, the second, optically transmissive optical element having a first surface on a first side facing the second light chamber and having a second surface opposite the first surface and forming a proximal end, the second, optically transmissive optical element further comprising a first, anti-reflective coating on the second surface.

In a representative system embodiment, as mentioned above, the one or more light emitting diodes may further comprise: at least one first light emitting diode for emission of red light or for light emission in a first spectral range; at least one second light emitting diode for emission of green light or for light emission in a second spectral range; at least one third light emitting diode for emission of blue light or for light emission in a third spectral range; and at least one fourth light emitting diode for emission of white light or for light emission in a fourth spectral range.

In a representative system embodiment, each pixel light source may further comprise: a second, reflective coating covering at least part of the rear wall and at least part of the at least one side wall within the first light chamber.

In a representative system embodiment, each pixel light source may further comprise: a third, non-reflective coating covering at least part of the at least one side wall within the second light chamber.

In a representative system embodiment, each pixel light source may further comprise: a third, diffusing optical element coupled to the at least one side wall, the third optical element arranged between and spaced-apart from the illumination source and the first optical element.

In a representative system embodiment, for each pixel light source, the at least one side wall may further comprise: a plurality of side walls coupled to each other to form an elongated polygonal structure enclosing the first and second light chambers in a transverse dimension, and wherein the elongated polygonal structure, together with the rear wall and the second optical element, define a frustum selected from the group consisting of: a pyramidal frustum, a triangular frustum, a square frustum, a pentagonal frustum, a hexagonal frustum, a septagonal frustum, an octagonal frustum, a conical frustum, and combinations thereof.

In a representative system embodiment, the partially-spherical dome spans an angular range between about 120° to 240° measured from the convergent location.

In a representative system embodiment, each pixel light source of the plurality of pixel light sources subtends less than 10° of visual angle measured from the convergent location.

In a representative embodiment, the system may further comprise: an operator control panel coupled to the control and driver circuit for input of the selected stimulus protocol; and a subject interface coupled to the control and driver circuit.

A representative embodiment for method of using the pixel light source system with a subject is also disclosed, comprising: using the pixel light source system, generating light stimulation to any arbitrary or selected portion of the retina of an eye of the subject.

Another representative embodiment for method of using the pixel light source system with a subject is also disclosed, with one or more electrodes coupled to the subject or with the system further comprising a subject interface, the representative method embodiment comprising: using a first plurality of pixel light sources, generating light stimulation to any arbitrary or selected portion of the retina of an eye of the subject; receiving signals from the one or more electrodes, such as ERG or VEP signals, or from the subject interface; correlating the received signals with one or more locations of the first plurality of pixel light sources; and identifying one or more regions of the visual system of the subject based on the correlation. Alternatively to the use of electrodes, a subject may also provide a response, such as pressing a button, when stimulation is perceived.

In a representative embodiment, the method may further comprise: selectively and sequentially generating light stimulation to a plurality of selected portions of the retina of the eye of the subject; and evaluating one or more functional changes where a local therapeutic intervention has been introduced.

In a representative embodiment, the method may further comprise: diagnosing one or more identified regions of the visual system of the subject based on the correlation.

Another representative pixel light source system embodiment for a stimulus source for visual pathway testing is disclosed, with the representative pixel light source system embodiment comprising: a plurality of pixel light sources and a control and driver circuit coupled to the plurality of pixel light sources. In such a representative embodiment, the plurality of pixel light sources are coupled to each other to form a partially-spherical dome, each pixel light source arranged to emit light directed to a convergent location of the partially-spherical dome, and each pixel light source comprising: a plurality of optically opaque side walls arranged to form a frustum structure; a rear wall coupled to the plurality of optically opaque side walls, the rear wall forming a distal end of the frustum structure; an illumination source arranged at or adjacent the distal end, the illumination source comprising one or more light emitting diodes; a first, diffusing optical element coupled to the at least one side wall and spaced apart proximally from the illumination source to define a first light chamber; a second, optically transmissive optical element coupled to the at least one side wall and spaced apart proximally from the first optical element to define a second light chamber, the second, optically transmissive optical element having a first surface on a first side facing the second light chamber and having a second surface opposite the first surface and forming a proximal end, the second, optically transmissive optical element further comprising a first, anti-reflective coating on the second surface; a second, reflective coating covering at least part of the rear wall and at least part of the plurality of optically opaque side walls within the first light chamber; and a third, non-reflective coating covering at least part of the plurality of optically opaque side walls within the second light chamber. The control and driver circuit is coupled to the plurality of pixel light sources, and the control and driver circuit is adapted to implement a selected stimulus protocol to selectively energize each pixel light source of the plurality of pixel light sources.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which.

DETAILED DESCRIPTION OF REPRESENTATIVE EMBODIMENTS

Figure 1:
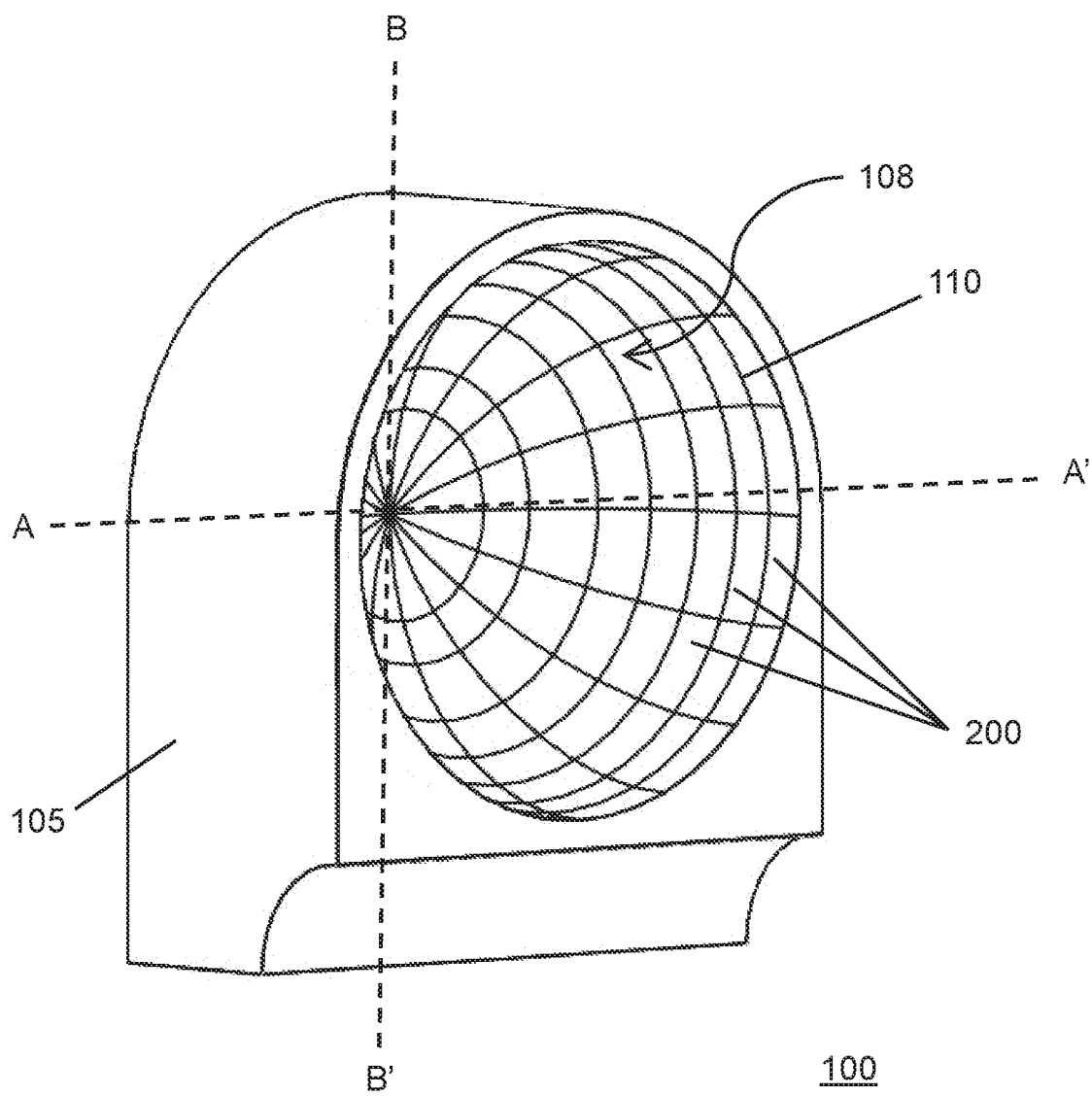
FIG. 1 is an isometric view diagram illustrating a representative system embodiment.

While the present invention is susceptible of embodiment in many different forms, there are shown in the drawings and will be described herein in detail specific exemplary embodiments thereof, with the understanding that the present disclosure is to be considered as an exemplification of the principles of the invention and is not intended to limit the invention to the specific embodiments illustrated. In this respect, before explaining at least one embodiment consistent with the present invention in detail, it is to be understood that the invention is not limited in its application to the details of construction and to the arrangements of components set forth above and below, illustrated in the drawings, or as described in the examples. Methods and apparatuses consistent with the present invention are capable of other embodiments and of being practiced and carried out in various ways. Also, it is to be understood that the phraseology and terminology employed herein, as well as the abstract included below, are for the purposes of description and should not be regarded as limiting.

As mentioned above and as discussed in greater detail below, the representative apparatus, system and method embodiments provide for a stimulus source which can provide selective and precise stimulation to any part of a retina, including both central and peripheral retina. The representative apparatus, system and method embodiments are also capable of generating any stimulus pattern for any type of ERG, visual-evoked potential and/or psychophysical testing for the retina, the optic nerve, and the visual cortex, and further avoid erroneous or unwanted stimulation or stimulation reflections of retinal or other areas which could interfere with the selected testing. The representative apparatus, system and method embodiments also provide an ERG, visual-evoked potential and/or psychophysical testing stimulus source which is able to identify the limits of the visual field in an objective manner, without requiring a skilled technician.

Especially significant, the representative apparatus, system and method embodiments provide for presenting a pattern visual stimulus on a curved surface that fills the visual field, where each pixel light source apparatus 200 providing a pixel in the pattern is capable of delivering a level of light that saturates the corresponding segment of the visual system. This further enables any type of electrophysiological and/or psychophysiological testing, including ERG, visual-evoked potential and/or psychophysical testing, which further can span the entire visual field.

As discussed in greater detail below, there are several significant new innovations supporting this new capability, including: the pixel light source apparatuses 200 arranged or arrayed to form a partially-spherical dome (or shell) 110; the design and configuration of the pixel light source apparatuses 200, which for a selected embodiment may be described generally as polygonal tube, light emitting diode ("LED")-based pixel light sources, with each pixel light source apparatus 200 including, for example, a high brightness LED (red, green, blue ("RGB"), and/or white) LED as an illumination source, and further having a front optical element (diffuser or window, respectively), of either a translucent light scattering material or a transmissive or transparent material that includes anti-reflection coatings tuned to the RGB wavelengths of the LEDs.

Figure 2A:
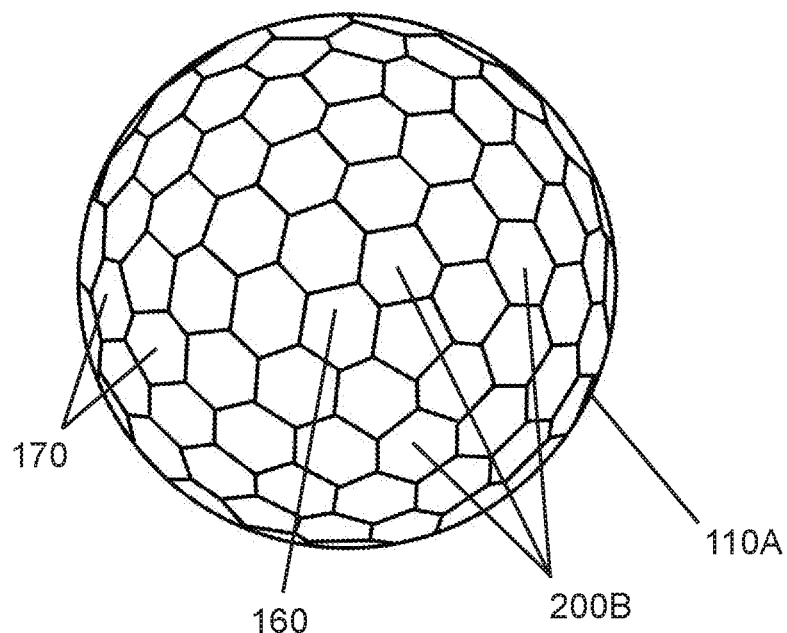
FIGS. 2A, 2B and 2C (collectively "FIG. 2") are front, plan view diagrams illustrating arrays of pixel light source apparatuses arranged to form partially-spherical domes (or shells) for a representative system embodiment.
Figure 2B:
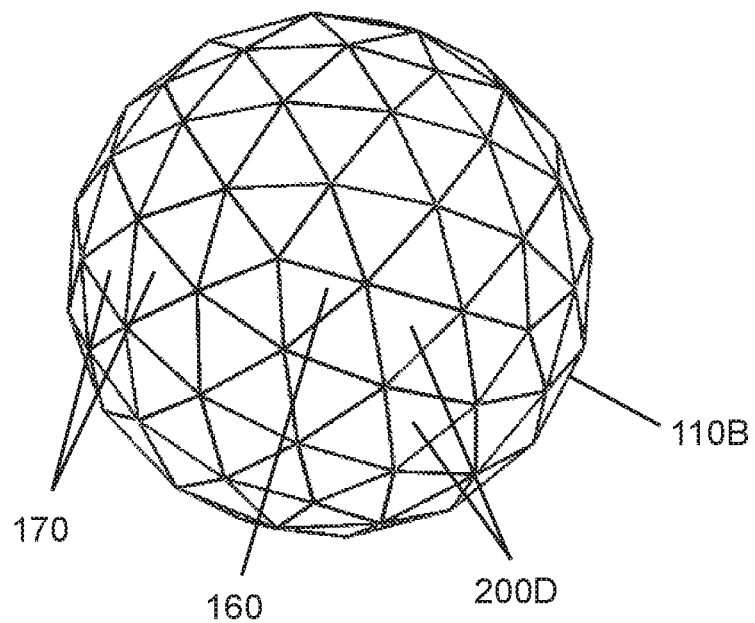
Figure 2C:
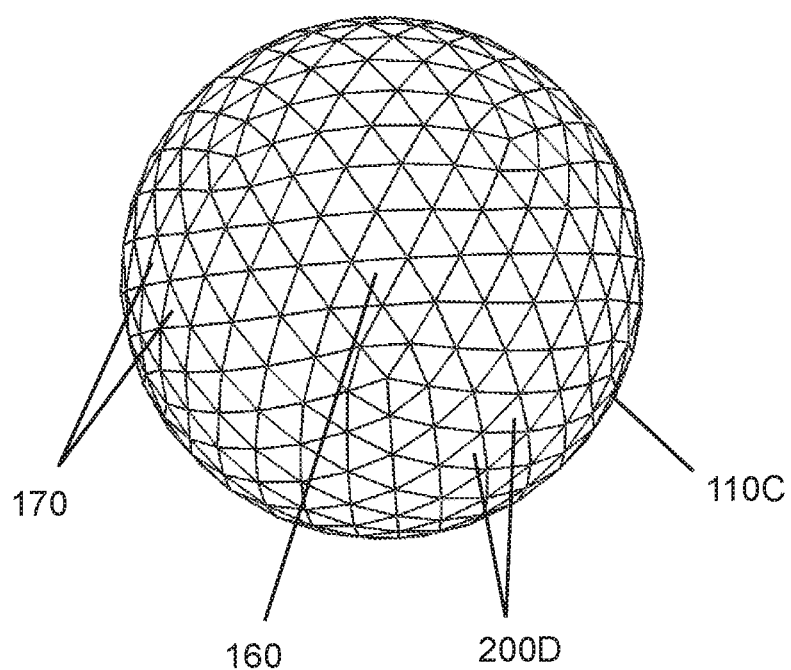
Figure 3:
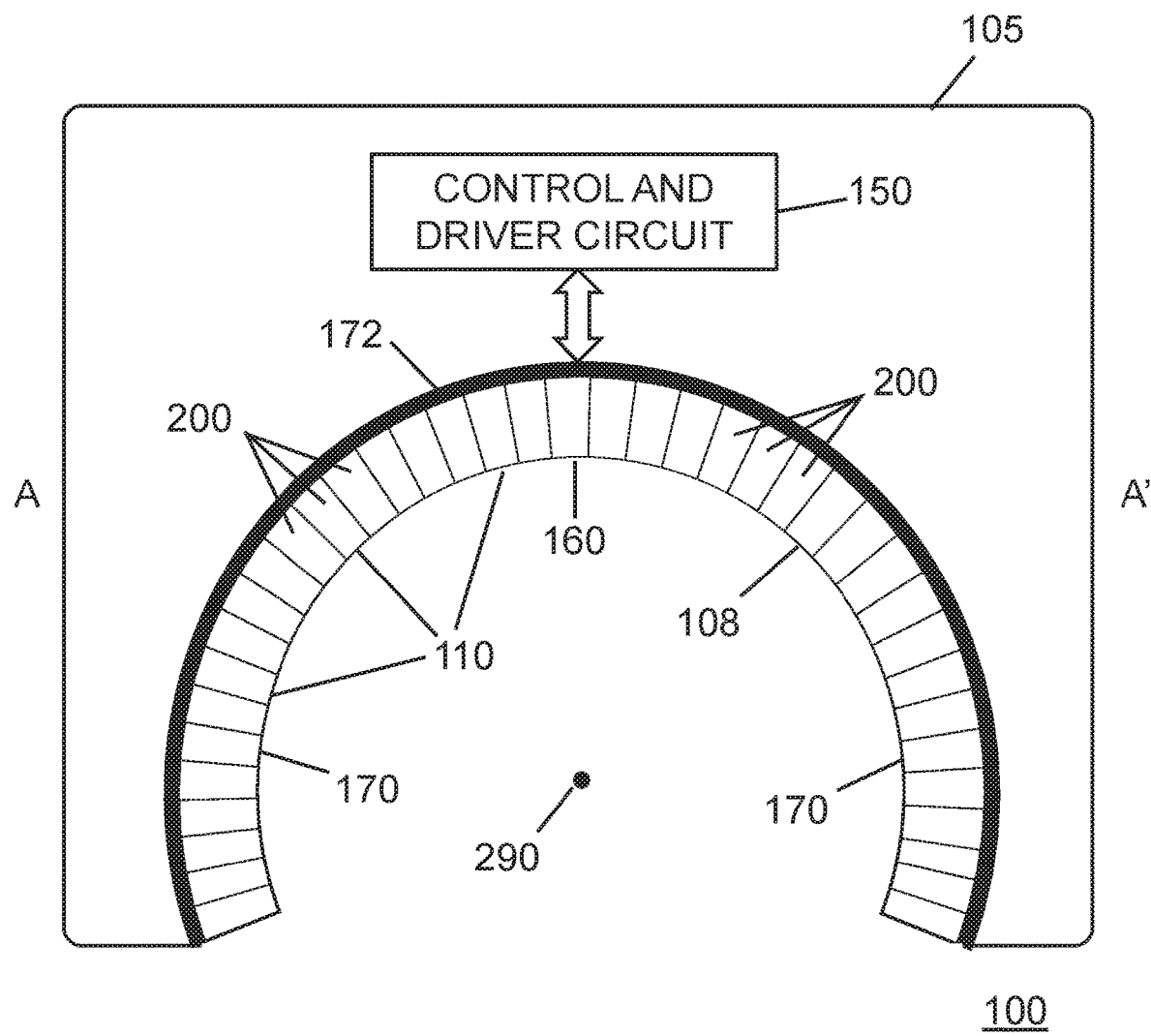
FIG. 3 is a first cross-sectional view diagram of the representative system embodiment of FIG. 1.
Figure 4:
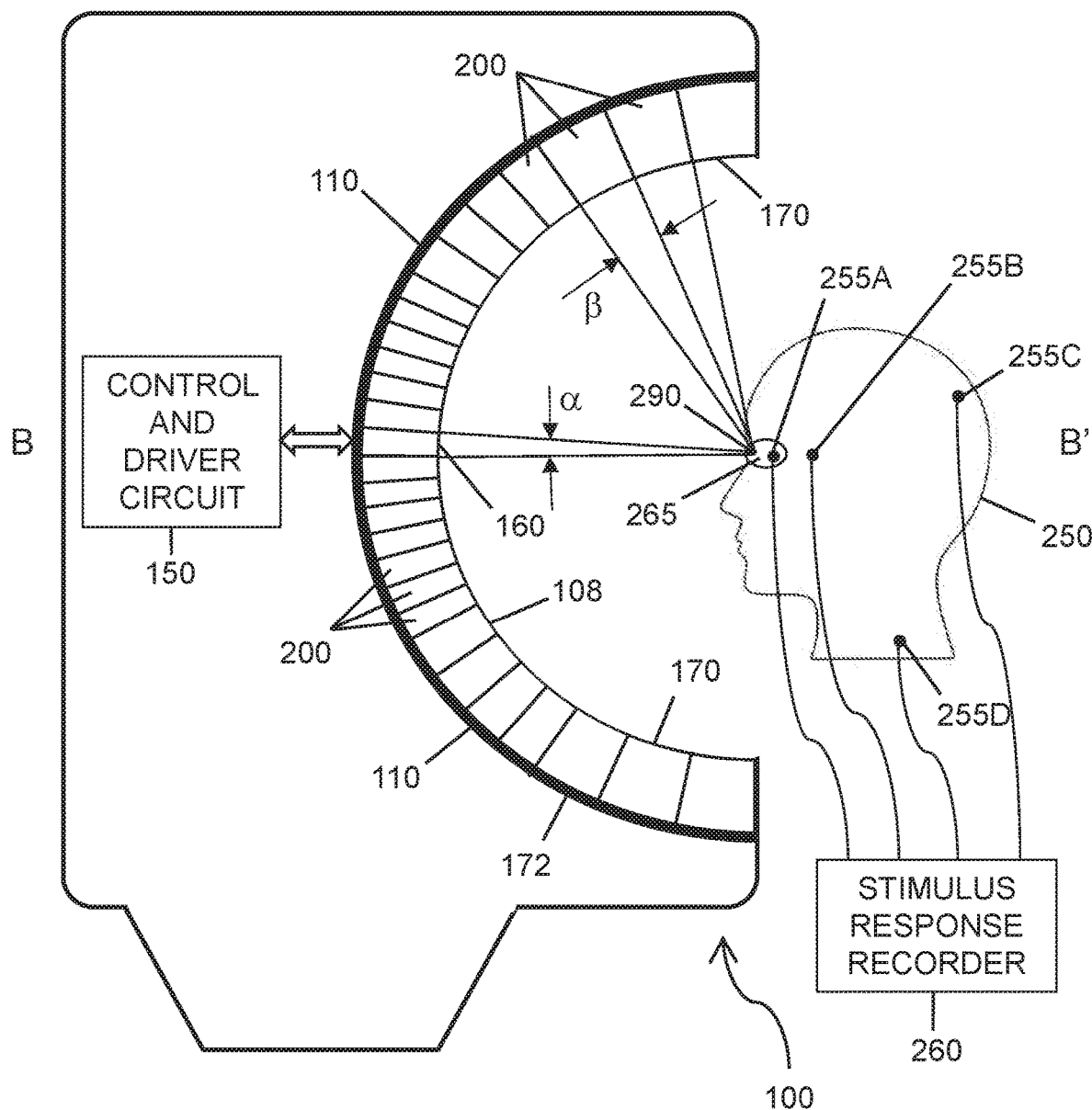
FIG. 4 is a second cross-sectional view diagram of the representative system embodiment of FIG. 1.
Figure 6:
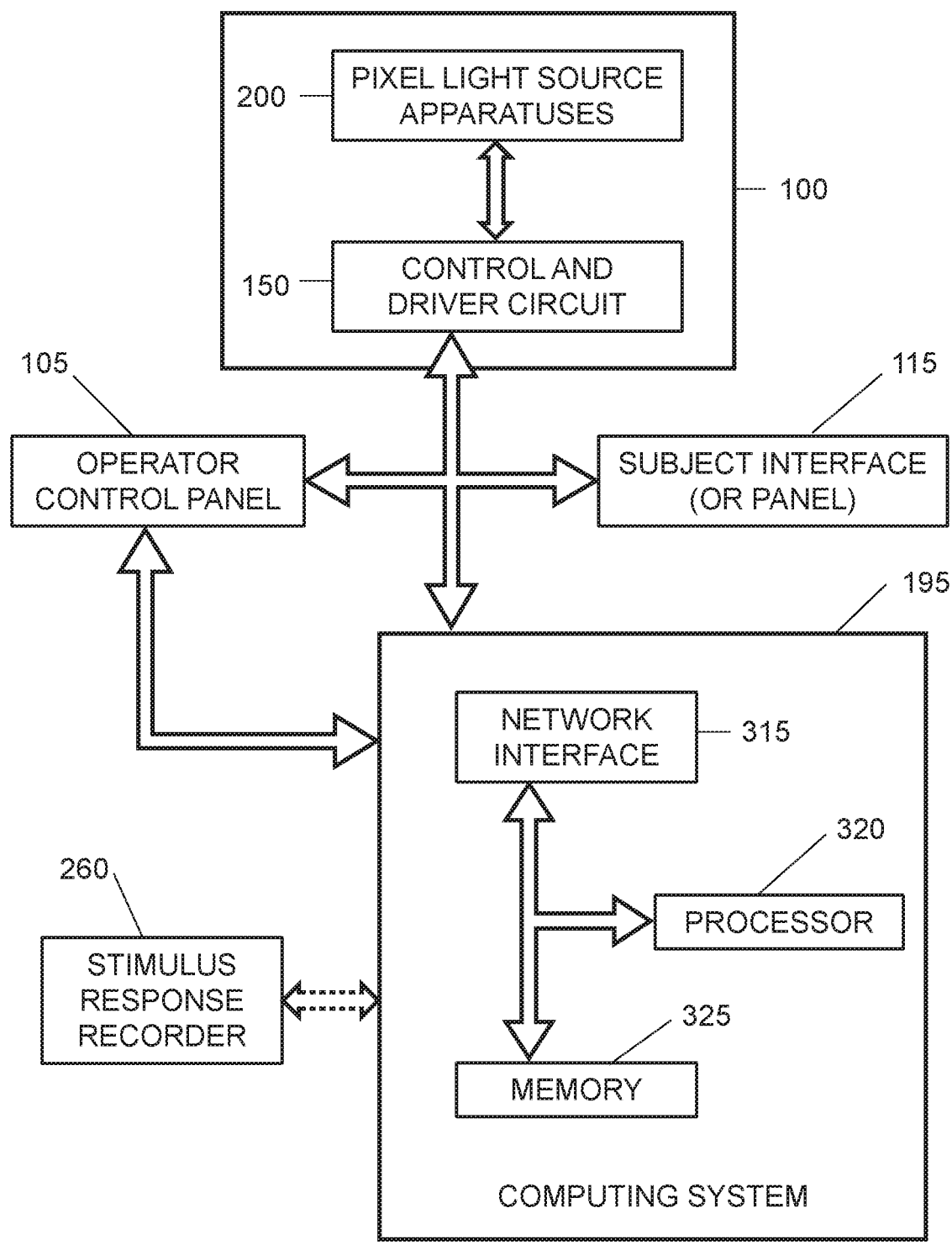
FIG. 6 is a block diagram of the representative system embodiment.

FIG. 1 is an isometric view diagram illustrating a representative system 100 embodiment. FIGS. 2A, 2B and 2C (collectively "FIG. 2) are front, plan view diagrams illustrating arrays of pixel light source apparatuses arranged to form a partially-spherical dome (or shell) 110 for a representative system embodiment. FIG. 3 is a first cross-sectional view (through the A-A' plane) diagram of the representative system 100 embodiment of FIG. 1. FIG. 4 is a second cross-sectional view (through the B-B' plane) diagram of the representative system embodiment of FIG. 1. FIG. 4 further illustrates a subject 250 having a plurality of recording electrodes 255 coupled to a stimulus response recorder 260. FIG. 6 is a block diagram of the representative system embodiment.

Referring to FIGS. 1-6, a representative system 100 comprises a housing 105, and within the housing 105, a plurality of pixel light source apparatuses 200 are arrayed or arranged to form a partially-spherical dome (or shell) 110, and a control and driver circuit 150 is provided to control and selectively energize each pixel light source apparatus 200 of the plurality of pixel light source apparatuses 200. Representative pixel light source apparatuses 200 and a representative control and driver circuit 150 are discussed in greater detail below with reference to FIGS. 7-16. The plurality of pixel light source apparatuses 200 may be held in place to form the partially-spherical dome (or shell) 110 using any means or mechanism as known in the art (not separately illustrated, such as welds, adhesives, screws, etc.), and additional structural components may also be utilized (such as a scaffolding 172 coupled to the plurality of pixel light source apparatuses 200 (illustrated in FIGS. 3 and 4), meshes, etc.), all for example and without limitation.

In one embodiment, the present disclosure details a novel stimulus source system 100, apparatus 200 and method for electroretinography (ERG), visual-evoked potential (VEP) and/or psychophysical testing. A partially-spherical dome (or shell) 110 of the system 100 may fill the visual field of the subject 250 when the subject 250, with an eye 265 positioned at the middle of the equator of the dome, looks into the center 160 of the interior, concave side 108 of the partially-spherical dome (or shell) 110 and fixates on a central point 160 (at the apex of the partially-spherical dome (or shell) 110). The partially-spherical dome (or shell) 110 is comprised of a plurality of pixel light source apparatuses 200, with each pixel light source apparatus as a part or facet of the interior, concave side (or surface) 108 of the partially-spherical dome (or shell) 110.

The partially-spherical dome (or shell) 110 is illustrated as partially-spherical or hemispherical in various embodiments as far as its macro-scale overall shape or configuration. Depending upon the curvatures, if any, of the pixel light source apparatuses 200 (and more specifically, of the second optical element 230 of the pixel light source apparatuses 200), the partially-spherical dome (or shell) 110 is not a smooth spherical surface, but is a truncated polyhedron approximating a partial sphere (or, equivalently, a faceted partial sphere), as illustrated, such as a geodesic hemisphere or dome, for example.

In addition, the partially-spherical dome (or shell) 110 may have any orientation (horizontal, vertical (as shown in FIG. 1), or any orientation in between horizontal or vertical), such as to accommodate any selected orientation of the subject 250. The partially-spherical dome (or shell) 110 also may be asymmetric (as discussed below), and also may be rotatable into any of a plurality of positions or orientations, such as to align properly with a subject 250. This is also important for use and application of the system 100 with non-human subjects.

As illustrated in FIG. 6, for completeness of the description of the representative system 100, the control and driver circuit 150 is generally coupled to an operator control panel 105 and to a subject interface (or panel) 115, and also may be coupled to a computing system 195. The operator control panel 105 may be implemented as known in the art for entry of control data (e.g., selection of an ERG, visual-evoked potential and/or psychophysical testing protocol) into the control and driver circuit 150, such as a graphical user interface. A computing system 195 (which also may be implemented as known in the art) may also be coupled to the control and driver circuit 150, either directly or via the operator control panel 105. The subject interface (or panel) 115 may be implemented as known in the art and merely provides a mechanism for a subject response if needed for a particular visual pathway test, such as a button to be pressed when the subject sees light during a test. The operator control panel 105 and/or computing system 195 are typically utilized for entry of various illumination parameters for a selected stimulus or stimulation protocol (discussed below). In addition, the computing system 195, which also may be coupled to receive ERG, visual-evoked potential and/or psychophysical testing response signals or data from a stimulus response recorder 260 (discussed below), may and generally is involved in performance of part of the representative method embodiment, such as to correlate the received ERG signals with the number and location of the plurality of pixel light source apparatuses 200 which may have been illuminated during the selected stimulus protocol, and to identify corresponding regions of the visual system, such as those which may be damaged, diseased, or otherwise functioning improperly.

The computing system 195 generally comprises a processor 320, a memory 325, and a network interface 315, among other components. The processor 320, the memory 325, and the network interface 315 are described in greater detail below. The computing system 195 is typically programed to provide a selected stimulation protocol to the system 100, and to perform various correlation and diagnostic steps of the claimed method, as discussed in greater detail below and further with reference to FIG. 17

As illustrated, the representative system 100 comprises a luminous, partially-spherical dome (or shell) 110 comprised of a plurality of pixel light source apparatuses 200. When selectively energized, each pixel light source apparatus 200 will emit a generally or substantially collimated light beam, into the eye 265 of a subject 250. Any selected constant or variable density of the pixel light source apparatuses 200 may be utilized within the partially-spherical dome (or shell) 110. For example, a greater number of pixel light source apparatuses 200 per unit area may be arrayed toward the center 160 of the partially-spherical dome (or shell) 110, and a fewer number of pixel light source apparatuses 200 per unit area may be arrayed toward the periphery 170 of the partially-spherical dome (or shell) 110, for example and without limitation.

Those having skill in the art will recognize that depending upon the number and density of the pixel light source apparatuses 200 utilized within the partially-spherical dome (or shell) 110, the variation of the number and density of the pixel light source apparatuses 200 in different parts of the partially-spherical dome (or shell) 110 (e.g., center 160 or periphery 170), and the corresponding size (or width in the transverse dimension) of the various pixel light source apparatuses 200, the visual angle (e.g., $\alpha$ or $\beta$) subtended by the light provided by each pixel light source apparatus 200 will vary accordingly, providing a smaller visual angle where there is a greater density of pixel light source apparatuses 200, and a greater visual angle where there is a lower density of pixel light source apparatuses 200. In the representative system 100, the pixel light source apparatuses 200 are generally shaped to efficiently tile and form the entire partially-spherical dome (or shell) 110, with each pixel light source apparatus 200 subtending a comparatively small (e.g., approximately one to ten degrees of visual angle) portion of the partially-spherical dome (or shell) 110. For example, each pixel light source of the plurality of pixel light source apparatus may subtend less than 10° of visual angle measured from a singular convergent location (position or point) 290, or more particularly, may subtend less than 5° of visual angle measured from a singular convergent location (position or point) 290, or more particularly, may subtend less than 4° of visual angle measured from the singular convergent location 290, or more particularly, may subtend less than 3° of visual angle measured from the singular convergent location 290, or more particularly, may subtend less than 2° of visual angle measured from the singular convergent location 290, or more particularly, may subtend less than 1° of visual angle measured from the singular convergent location 290, and so on.

Continuing with the example, in one embodiment, the pixel light source apparatuses 200 may be of varying sizes. For example, as an option, the sizes of the pixel light source apparatuses 200 could vary inversely with the density of cells in the associated portion of the retina. This may result in small pixel light source apparatuses 200 in the center 160 of the partially-spherical dome (or shell) 110 to provide finer light probe resolution where cell density is high in the retina, gradually changing to larger pixel light source apparatuses 200 in the periphery 170 of the partially-spherical dome (or shell) 110 to provide correspondingly lower resolution where cell density is lower.

Several of these variations are illustrated in FIGS. 2A, 2B and 2C. As illustrated in FIG. 2A, a plurality of pixel light source apparatuses 200B (illustrated in FIGS. 9 and 10), which have hexagonal cross-sections, are arranged (or tiled) to form a partially-spherical dome (or shell) 110A for a representative system 100 embodiment. As illustrated in FIG. 2B, a plurality of pixel light source apparatuses 200D (illustrated in FIGS. 13 and 14), which have triangular cross-sections, are arranged (or tiled) to form a partially-spherical dome (or shell) 110B for a representative system 100 embodiment. As illustrated in FIG. 2C, and in comparison to the partially-spherical dome (or shell) 110B of FIG. 2B, a greater number of pixel light source apparatuses 200D, which also have comparatively smaller triangular cross-sections, are arranged (or tiled) to form a partially-spherical dome (or shell) 110C having a higher density of pixel light source apparatuses 200D to provide finer light probe resolution for a representative system 100 embodiment. As discussed in greater detail below, any and all combinations of such pixel light source apparatuses 200 arrayed to form a partially-spherical dome (or shell) 110 are within the scope of the disclosure.

Within the partially-spherical dome (or shell) 110, each of the plurality of pixel light source apparatuses 200 may be individually selected and energized using the control and driver circuit 150, using any selected addressing or selection. For example and without limitation, column and row addressing or selection may be utilized, with the plurality of pixel light source apparatuses 200 arranged in a plurality of annular rows and a plurality of radial columns within the partially-spherical dome (or shell) 110.

Figure 5:
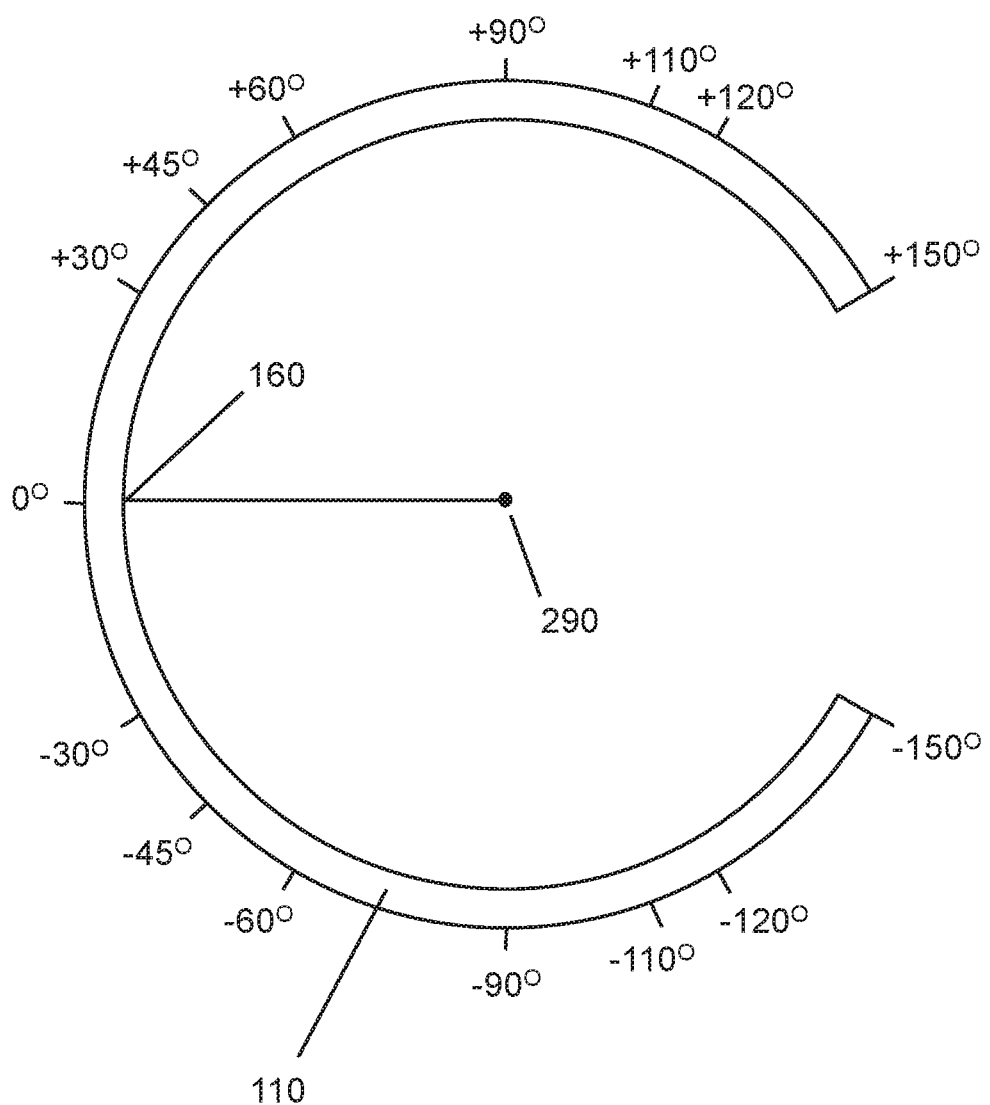
FIG. 5 is a graphical diagram illustrating a plurality of angular or circumferential spans in any dimension of a partially-spherical dome (or shell) for a representative system embodiment.

Those having skill in the art will recognize that that the partially-spherical dome (or shell) 110 may have any of a plurality of different shapes and a plurality of different angular or circumferential spans in any dimension. FIG. 5 is a graphical diagram illustrating a plurality of circumferential spans in any dimension of a partially-spherical dome (or shell) for a representative system embodiment. A line from the convergent location (position or point) 290 to the center (or apex) 160 of the partially-spherical dome (or shell) 110 is considered to be zero degrees, and is the "zero degree reference" for all measurements or determinations herein. As illustrated in FIG. 5, the partially-spherical dome (or shell) 110 will typically have any angular or circumferential span, in any dimension, from about 120° to about 300° (in "full" angles) or equivalently about 60° to about 150° (in "half" angles), and may be symmetrical or asymmetrical, as described below.

For example and without limitation, with zero degrees being defined as being a line from the convergent location 290 to the center (or apex) 160 of the partially-spherical dome (or shell) 110), which is the same as or parallel to the optical axis of the eye 265 as illustrated, then the edges of the partially-spherical dome (or shell) 110) could be located anywhere from about 60 degrees (in all radial directions, i.e., a spherical section that is less than half a sphere) to about 120 degrees (in all radial directions, i.e., a spherical section that is more than half a sphere), or it could be asymmetrical, being, for example, about 60 degrees in the nasal direction and about 120 degrees in the temporal direction and transitioning from 60 degrees to 120 degrees along any arbitrary curve between the nasal and temporal directions.

Also for example and without limitation, the partially-spherical dome (or shell) 110 may be, but may not be and is not required to be, a symmetric hemisphere spanning a full 180° in two dimensions (in "full" angles, as measured or determined from the zero degree reference). Rather, in representative embodiments, the partially-spherical dome (or shell) 110 is dimensioned to accommodate stimulation and testing of the entire visual field. This is illustrated in FIGS. 3 and 4. For example, as illustrated in FIG. 4, the representative partially-spherical dome (or shell) 110 spans 180° in the vertical (or up-down, top-bottom) dimension, even though a typical visual (peripheral) field may not detect a full 180° in this direction. Also for example, as illustrated in FIG. 3, the representative partially-spherical dome (or shell) 110 spans 220° in the horizontal (or lateral, right-left) dimension (also in "full" angles, as measured or determined from the zero degree reference), because a typical visual (peripheral) field is capable of detecting objects in a wider peripheral span than 180° in this direction. In addition, the visual fields may be asymmetric in other ways, e.g., the more medial visual fields (nasal direction or toward a subject's nose) is also generally more limited compared to the more lateral (temporal) visual fields, as mentioned above. Accordingly, for a representative system 100 to accommodate both the left and right eyes 265 of a subject 250, the partially-spherical dome (or shell) 110 may have some symmetry, e.g., lateral symmetry, vertical symmetry, and potentially may also have rotational symmetry. Otherwise, the partially-spherical dome (or shell) 110) may be further asymmetric laterally, and be rotated 180° when testing is switched from one eye (left or right) to the other eye (right or left).

By having the pixel light source apparatuses 200 form the partially-spherical dome (or shell) 110 spanning a full 180° vertically (or 90° using "half" angles) and potentially even more laterally (or horizontally), e.g., 220° (or 110° using "half" angles), however, the function of the entire visual pathway may be tested and probed, as sufficient pixel light source apparatuses 200 are then available to selectively illuminate any and all parts of the retinas of the eyes 265 of the subject 250. Accordingly, as used herein, the plurality of pixel light source apparatuses 200 may form a partially-spherical dome (or shell) 110 spanning a range (in full angles) between about 60° to 300°, or more particularly between about 90° to 240°, or more particularly between about 100° to 220°, or more particularly between about 120° to 220°, or more particularly between about 130° to 220°, or more particularly between about 140° to 220°, or more particularly between about 150° to 220°, or more particularly between about 160° to 220°, or more particularly between about 170° to 220°, or more particularly between about 180° to 220°, in any dimension, for example and without limitation (in "full" angles, as measured or determined from the zero degree reference), for example and without limitation. In addition, the partially-spherical dome (or shell) 110 may also be implemented to by asymmetric, such as spanning a greater number of degrees in one dimension (e.g., horizontally) compared to another dimension (e.g., vertically), and/or vice-versa.

In a representative system 100, the partially-spherical dome (or shell) 110 may be as large as 60 cm in diameter or larger, e.g., typically having a radius about equal to the shortest distance of focus for a typical adult, for a human subject, such as about fourteen inches, for example and without limitation. An array of pixel light source apparatuses 200, adjacent to one another, is disposed in an arrangement to form the luminous, partially-spherical dome (or shell) 110. For testing, a subject 250 is positioned or aligned in front of the partially-spherical dome (or shell) 110, facing the interior of the partially-spherical dome (or shell) 110, such that the eye 265 of the subject 250 is about at the convergent location 290, with the individual subject 250 generally looking at the center 160 of the partially-spherical dome (or shell) 110, in such a manner as to allow the testing of the entire field of vision, as shown in cross-section in FIG. 4. This alignment allows the image of each pixel light source apparatus 200 to be focused by the optics of the eye 265 of the subject 250 and stimulate a corresponding part of the retina of the eye 265 of the subject 250. With the partially-spherical dome (or shell) 110) being sized to have a radius on the order of 30 cm, the optics of the eye 265 can cast the image of the pixels on the retina in focus. A beam being directed into the eye 265, however, does not need to be at any particular distance to be cast on the retina as a spot, as long as the refraction of the cornea is eliminated or accommodated (e.g., by use of a flat window coupled to the cornea, for example and without limitation). Accordingly, the partially-spherical dome (or shell) 110 may have a wide range of shapes and sizes, any and all of which are within the scope of the disclosure.

Also as illustrated in FIG. 4, a plurality of recording electrodes 255 are attached to the subject 250, and further have electrode leads coupled to a stimulus response recorder 260, for receiving stimulus response signals following stimulation for ERG, visual-evoked potential and/or perimetry testing, for example. As illustrated for ERG recording, a recording electrode 255A contacts the eye 265 or the skin near the eye 265, another, "reference" recording electrode 255B contacts the skin of the subject 250 near the eye 265 (e.g., temple, or ear), and another "ground" recording electrode 255D contacts the skin of the subject near the neck of the subject 250 (or sometimes near the eye 265). For VEP recording, a recording electrode 255C contacts the skin near or over the visual cortex of the subject 250, the "reference" recording electrode 255B would contact the skin of the subject 250 at the ear, and the "ground" recording electrode 255D would also contact the skin of the subject near the neck of the subject 250. Any type or kind of recording electrodes 255 and stimulus response recorders 260 which are known or become known may be utilized with the representative system 100. The stimulus response may be recorded using standard stimulus response recording techniques.

While illustrated with a human subject 250, those having skill in the art will recognize that the representative system 100 may be utilized for visual pathway testing and diagnosis with any type of subject, including non-human primates, rabbits, pigs, mice, rats, cats, and zebra fish, for example and without limitation. The representative system 100, therefore, is also especially suited for use in research studies involving such non-human subjects, especially where perimetry stimulus protocols can be used in conjunction with electrophysiological recording instead of the typical behavioral recording.

As discussed in greater detail below, in a representative embodiment, the partially-spherical dome (or shell) 110 may comprise an array of individual pixel light source apparatuses 200, where each individual pixel light source apparatus 200 may emit the same ranges of wavelengths of light (e.g., white, red, blue, or green) or a plurality of different ranges of wavelengths of light (e.g., white, red, blue, or green), or any combination thereof. For example, each pixel light source apparatus 200 may have a plurality of selectable illumination sources 205, each having a different range of wavelengths of light (e.g., white, red, blue, or green). Alternatively, a first pixel light source apparatus 200 may have a single illumination source 205 having a first selected range of wavelengths of light (e.g., white), a second pixel light source apparatus 200 may have a single illumination source 205 having a second selected range of wavelengths of light (e.g., red), a third pixel light source apparatus 200 may have a single illumination source 205 having a third selected range of wavelengths of light (e.g., blue), a fourth pixel light source apparatus 200 may have a single illumination source 205 having a fourth selected range of wavelengths of light (e.g., green), and so on. This may allow a combination of individual light sources 205 to be used together to produce a mixture of wavelengths of light, thereby producing different colors of light, for example and without limitation.

Using the control and driver circuit 150, each of the pixel light source apparatuses 200 may be illuminated or turned on individually or in any combination, and the luminance of each pixel light source apparatus 200 may also be individually controllable. This flexibility of the representative system 100 in being able to light different portions of the partially-spherical dome (or shell) 110, and in being able to have varying degrees of illumination, allows the user to probe any arbitrary section of the retina, by providing a visual stimulus to that part of the retina by illuminating the corresponding pixel light source apparatuses 200 on the partially-spherical dome (or shell) 110, thereby ascertaining a measure of local health. Accordingly, the representative system 100 adds a significant new dimension to ERG testing, i.e., spatial selectivity. The representative system 100 also may also be programmed to present the kind of stimulus used in the multi-focal ERG test, thereby expanding that test from evaluating the central retina only to evaluating the entire retina.

Any type of visual pathway testing may be performed by the representative system 100, which may now be extended to probe the entire visual field and no longer limited to the central visual field, including without limitation:

(1) Electroretinogram (ERG) protocols, including: (a) Patterned Stimulus protocols such as focal ERG, using single small spots of white light; multi-focal ERG (mfERG), using pseudo-random patterns of flashing pixels; chromatic focal ERG, using single small spots of light of any color; pattern ERG (pERG), using alternating checks or bars; (b) Full-field (Ganzfeld) stimulus protocols such as flash ERG, using a brief white flash; paired-flash ERG, using a test flash followed by a bright probe flash; flicker ERG, using a series of brief white flashes; scotopic threshold response (STR), using a dim white flash; photopic negative response (PhNR), using a blue flash on red background; step response, using a fast change in luminance, up or down; ON response, using a rapid-on followed by slow decrease in luminance; OFF response, using a slow increase in luminance followed by rapid-off; and chromatic, using flashes of any color.

(2) Visual-Evoked Potential (VEP) protocols, including: (a) Patterned Stimulus protocols such as focal VEP, using single small spots of white light; multi-focal VEP (mfVEP), using pseudo-random patterns of flashing pixels; chromatic focal VEP, using single small spots of light of any color; pattern VEP (pVEP), using alternating checks or bars; (b) Full-field (Ganzfeld) stimulus protocols such as flash VEP, using a brief white flash; paired-flash VEP, using a test flash followed by a bright probe flash; flicker VEP, using a series of brief white flashes; scotopic threshold response (STR), using a dim white flash; photopic negative response (PhNR), using a blue flash on red background; step response, using a fast change in luminance, up or down; ON response, using a rapid-on followed by slow decrease in luminance; OFF response, using a slow increase in luminance followed by rapid-off; and chromatic, using flashes of any color.

(3) Psychophysical Testing, including: (a) visual field/perimetry, using small spots of light of varying luminance presented at different locations; and (b) contrast sensitivity, using spots or patterns (e.g. bars) of light of varying luminance on backgrounds of varying luminance.

Especially novel, the representative system 100 may perform completely new types of ERG, visual-evoked potential and/or psychophysical testing and diagnostics, which heretofore cannot be accomplished using any other device or system. For example, as a new type of patterned stimulus protocol, an ERG response may be recorded in the presence of an induced transient scotoma, accomplished by delivering a saturating, continuous luminance from a first, small cluster of a plurality of pixel light source apparatuses 200 to a corresponding portion of the retina (which then cannot respond to any further stimulus, and hence behaves like a scotoma or blind spot). Then during the delivery of this locally-saturating stimulus from the first plurality of pixel light source apparatuses 200, a second, different plurality of pixel light source apparatuses 200 present a brief flash of light to the remainder of the retina.

In addition, such testing is no longer limited to probing the entire retina uniformly, resulting in a response that represents the average response of the entire retina. The representative system 100 provides the capability to probe isolated areas of the retina with any of the full-field protocols. Any protocol to be utilized by the system 100, of a plurality of stimulation protocols, may be stored in a memory 125 and/or memory 325 and selected using the computing system 195 and/or the operator control panel 105.

Figure 7:
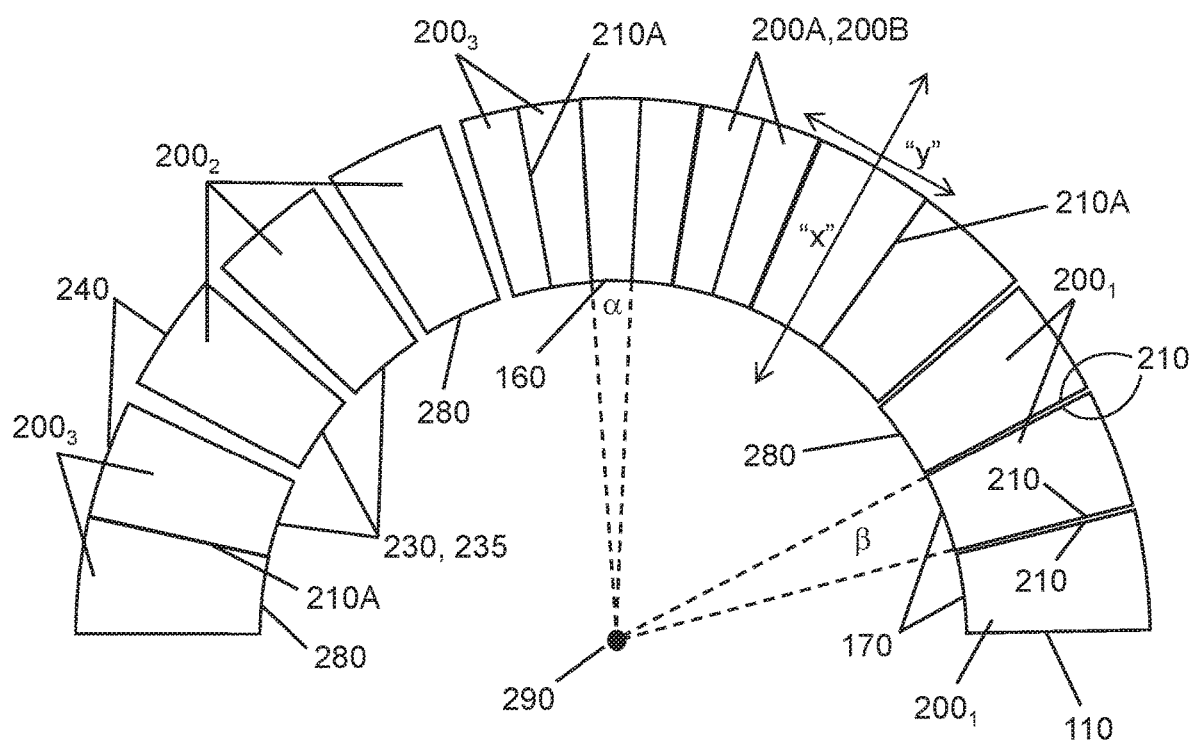
FIG. 7 is a first cross-sectional view diagram illustrating an array of pixel light source apparatuses arranged to form a partially-spherical dome (or shell) for a representative system embodiment.
Figure 8:
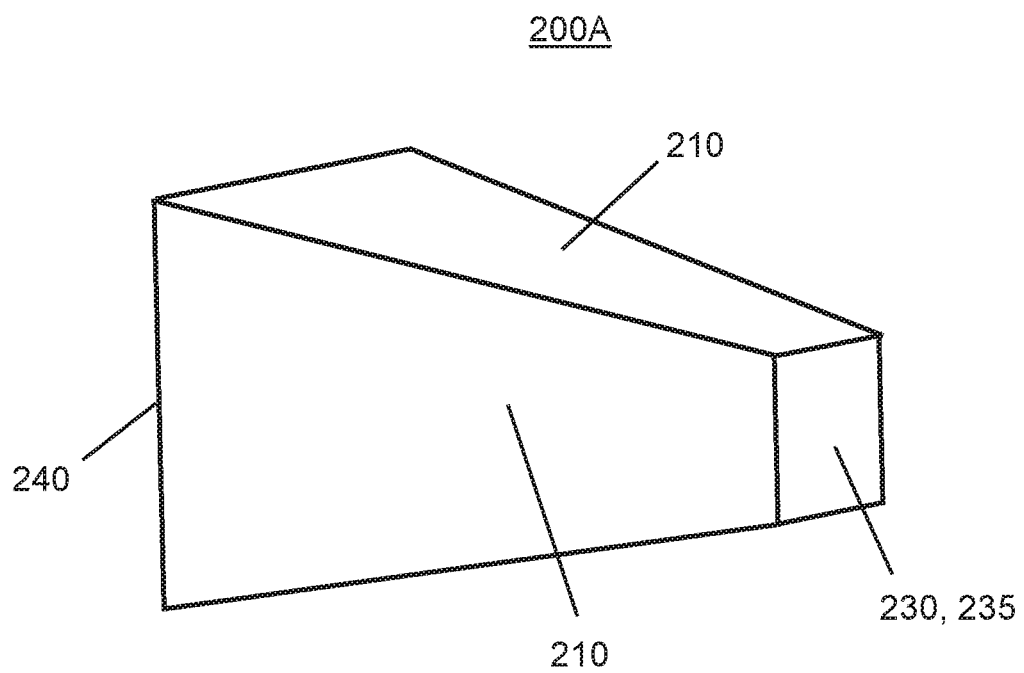
FIG. 8 is an isometric view diagram illustrating a representative first pixel light source apparatus embodiment.
Figure 9:
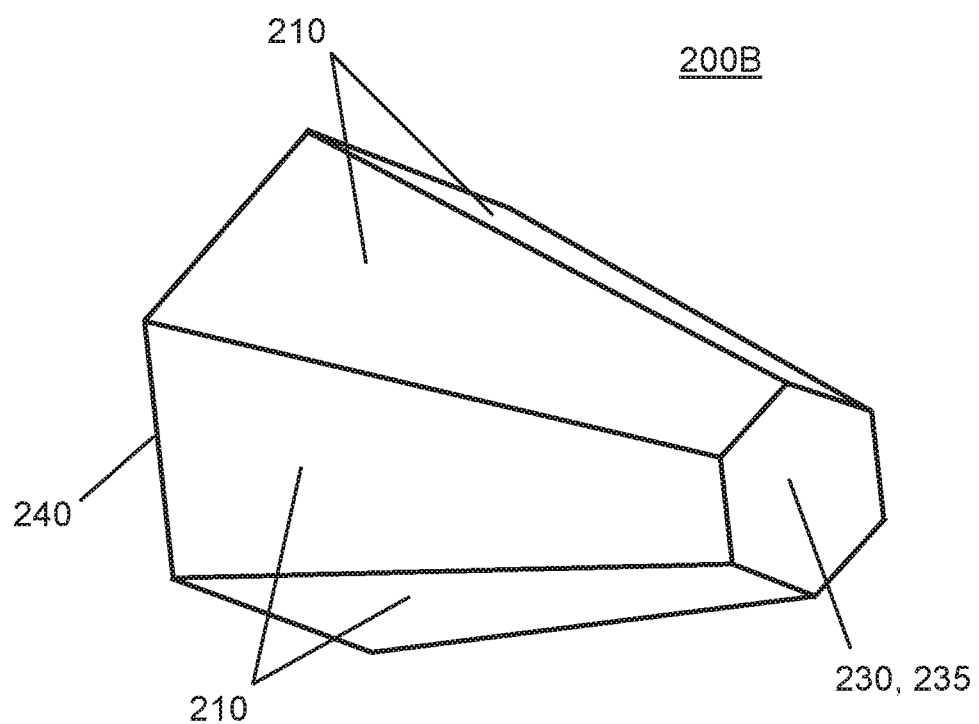
FIG. 9 is an isometric view diagram illustrating a representative second pixel light source apparatus embodiment.
Figure 10:
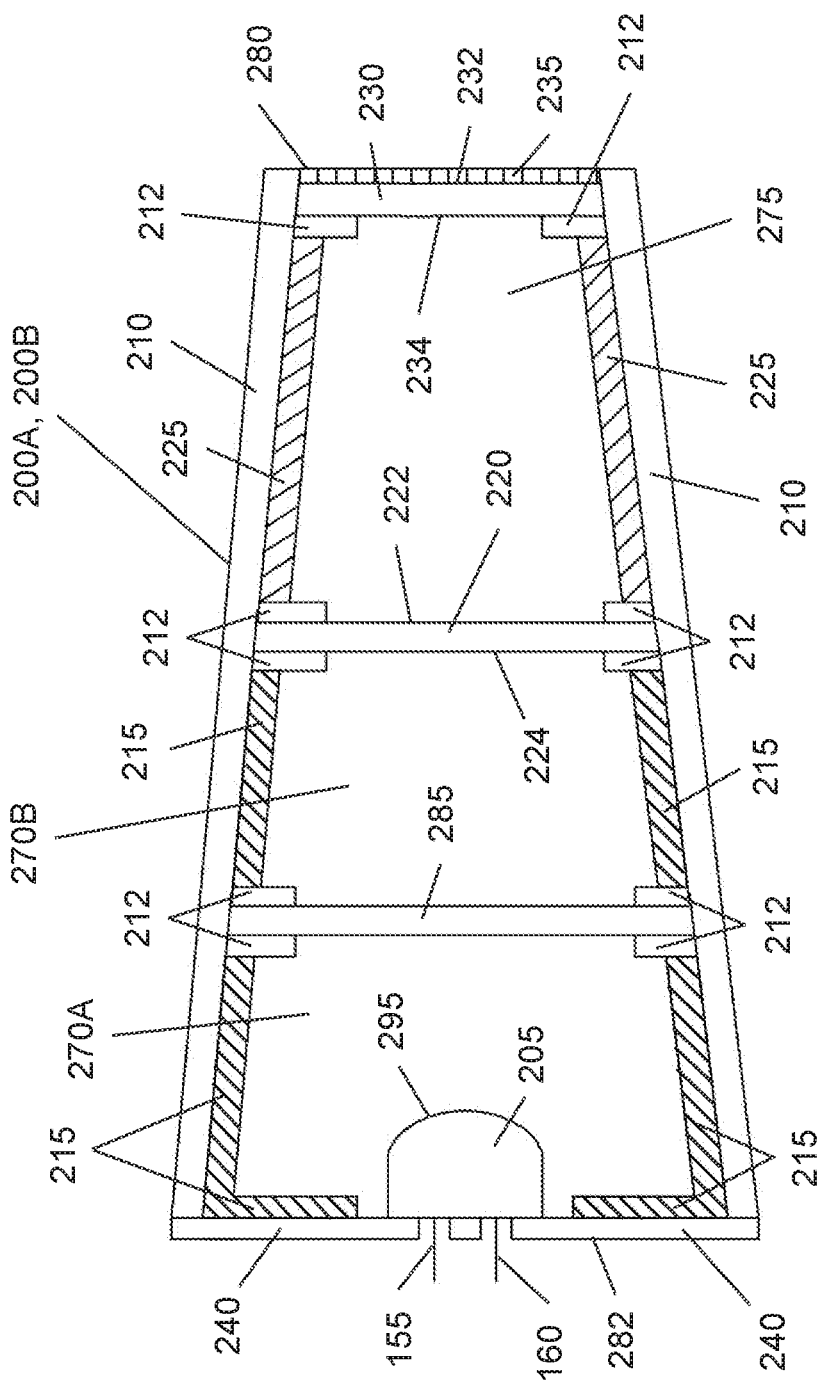
FIG. 10 is cross-sectional view diagram of the representative first and second pixel light source apparatus embodiments of FIGS. 8 and 9.
Figure 11:
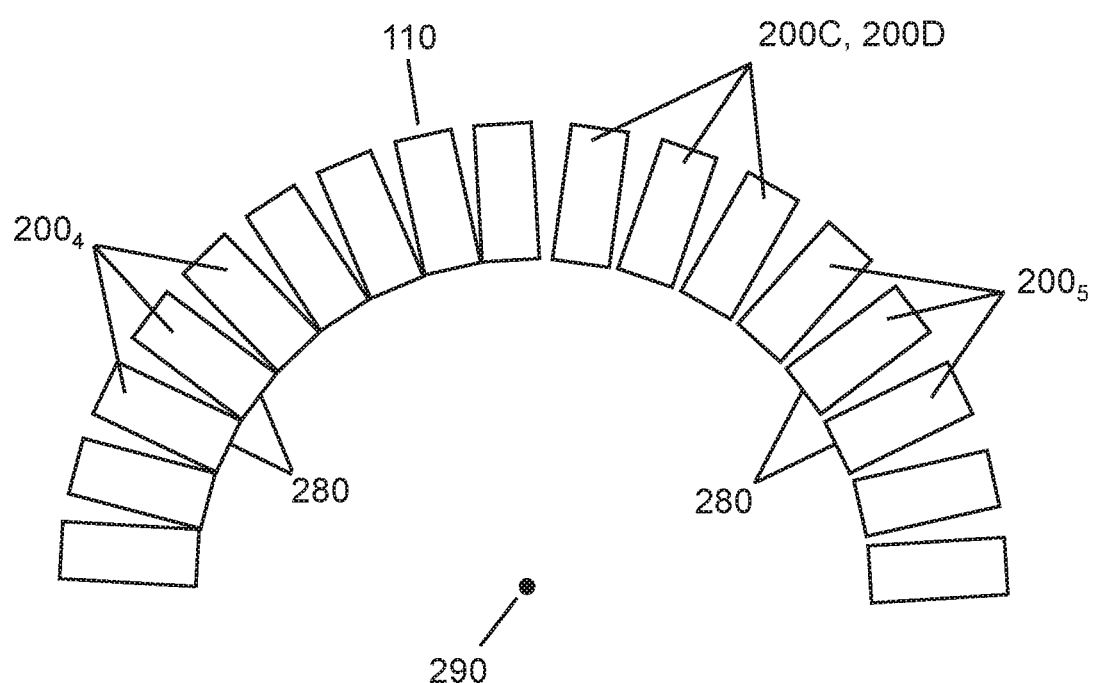
FIG. 11 is a second cross-sectional view diagram illustrating an array of pixel light source apparatuses arranged to form a partially-spherical dome (or shell) for a representative system embodiment.
Figure 12:
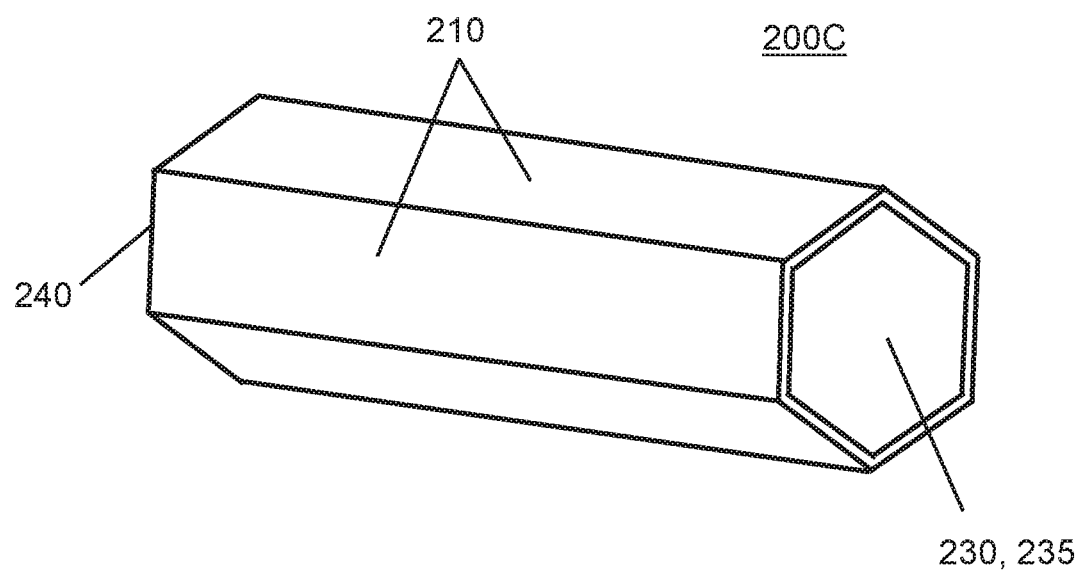
FIG. 12 is an isometric view diagram illustrating a representative third pixel light source apparatus embodiment.
Figure 13:
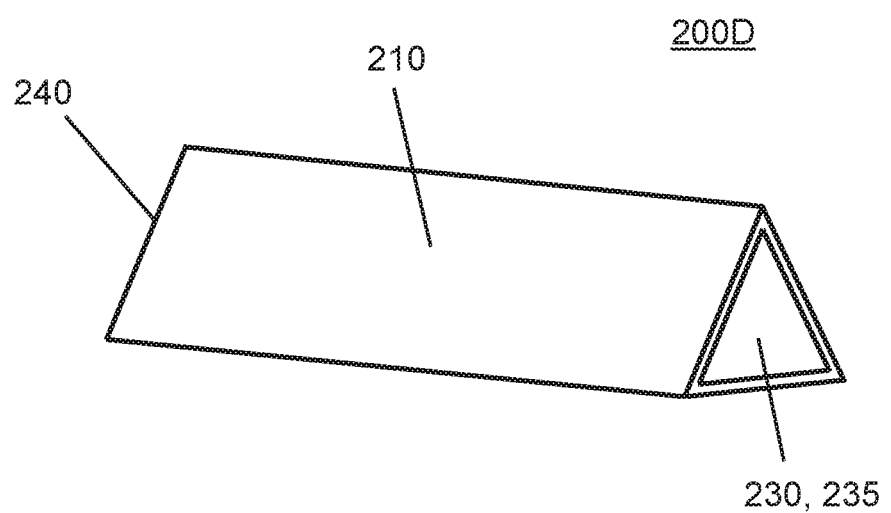
FIG. 13 is an isometric view diagram illustrating a representative fourth pixel light source apparatus embodiment.
Figure 14:
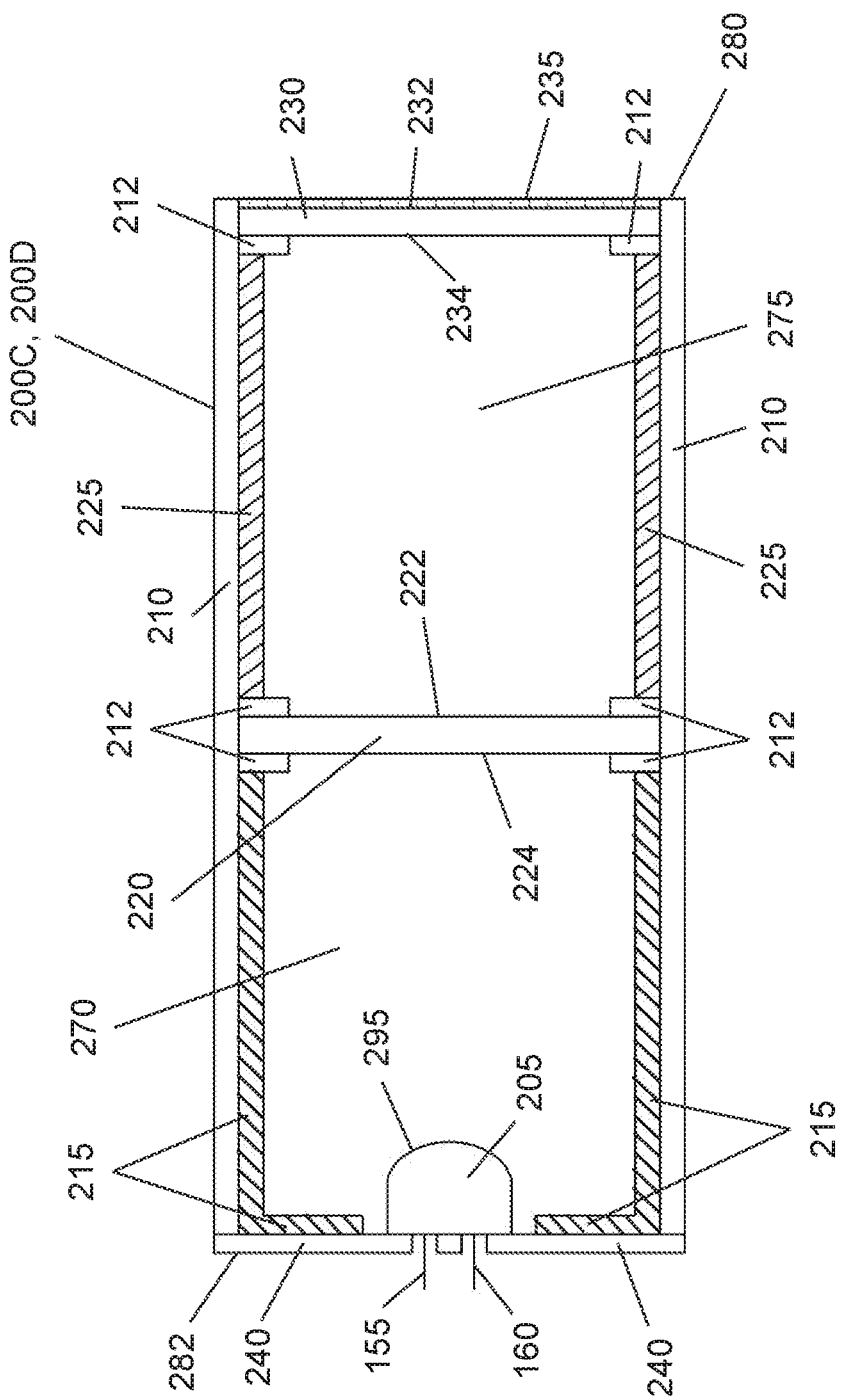
FIG. 14 is cross-sectional view diagram of the representative third and fourth pixel light source apparatus embodiments of FIGS. 12 and 13.

FIG. 7 is a first cross-sectional view diagram illustrating an array of pixel light source apparatuses 200A, 200B arranged to form a partially-spherical dome (or shell) 110 for a representative system 100 embodiment. FIG. 8 is an isometric view diagram illustrating a representative first pixel light source apparatus 200A embodiment. FIG. 9 is an isometric view diagram illustrating a representative second pixel light source apparatus 200B embodiment. FIG. 10 is cross-sectional view diagram of the representative first and second pixel light source apparatus 200A, 200B embodiments of FIGS. 8 and 9. FIG. 11 is a second cross-sectional view diagram illustrating an array of pixel light source apparatuses 200C, 200D arranged to form a partially-spherical dome (or shell) 110 for a representative system 100 embodiment. FIG. 12 is an isometric view diagram illustrating a representative third pixel light source apparatus 200C embodiment. FIG. 13 is an isometric view diagram illustrating a representative fourth pixel light source apparatus 200D embodiment. FIG. 14 is cross-sectional view diagram of the representative third and fourth pixel light source apparatus 200C, 200D embodiments of FIGS. 12 and 13.

Referring to FIGS. 7-14, each pixel light source apparatus 200 is generally elongated and/or tubular, and may be trapezoidal in longitudinal dimension or cross-section, such as illustrated in FIG. 10 for the representative first and second pixel light source apparatus 200A, 200B embodiments of FIGS. 8 and 9, or may be rectangular in longitudinal dimension or cross-section, such as illustrated in FIG. 14 for the representative third and fourth pixel light source apparatus 200C, 200D embodiments of FIGS. 12 and 13, for example and without limitation. While referred to as elongated or tubular, the pixel light source apparatuses 200 may have any transverse shape or cross-section, such as polygonal, in addition to circular or elliptical, for example and without limitation.

Each pixel light source apparatus 200 comprises one or more side walls 210, and may also include a rear or distal wall 240 (which may be solid or may be perforated, such as for air flow and cooling, and which forms a first, rear or distal end 282 of the pixel light source apparatus 200), which may be considered to form a housing or a cell. The side walls 210 and the rear or distal wall 240 may be integrally-formed or may be coupled to each other using any mechanism which is known or becomes known, such as tabs, slots, adhesives, welds, screws, etc., for example and without limitation (not separately illustrated), and/or may be held in place using any of the structures of the partially-spherical dome (or shell) 110 discussed above. For example, the scaffolding 172 may be coupled to the rear or distal wall 240, and in turn, the rear or distal wall 240 is coupled to the one or more side walls 210.

Each pixel light source apparatus 200 further comprises an illumination source 205 arranged or disposed at or near the distal end of the pixel light source apparatus 200, such as one or more light emitting diodes as mentioned above; a first, diffusing internal optical element 220 arranged or disposed to be spaced-apart proximally from the illumination source 205 and coupled to the side walls 210 to form a first, rear or distal light chamber 270 (which also may be further divided into parts, as 270A and 270B); and a second optical element 230 forming a second, front or proximal end 280 of the pixel light source apparatus 200, with the second optical element 230 arranged or disposed to be spaced-apart further proximally from the illumination source 205 and arranged or disposed to be spaced-apart proximally from the first, internal optical element 220, and also coupled to the side walls 210 to form a second, front or proximal light chamber 275. Positive and negative electrical leads or wires 155, 160 are also coupled to the illumination source 205 for coupling to the control and driver circuit 150 for selectively providing power to and energizing the illumination source 205. The illumination source 205, the rear or distal wall 240, the first, internal optical element 220, the second optical element 230 (and third optical element 285) may be held in place or attached to the side walls 210 using any mechanism which is known or becomes known, such as tabs 212, or slots, adhesives, welds, screws, etc., for example and without limitation (not separately illustrated).

In a representative embodiment, the second optical element 230 of the pixel light source apparatus 200 has first and second surfaces 232 and 234, with the first surface 232 facing the interior space defined or enclosed by the partially-spherical dome (or shell) 110, and the second surface 234 facing the second, front or proximal light chamber 275. There are several available embodiments of the second optical element 230 within the scope of the disclosure. In a first representative embodiment, the second optical element 230 is substantially optically transmissive, transparent or clear, and the pixel light source apparatus 200 further includes or comprises a first, anti-reflective coating 235 on the first surface 232 of the second optical element 230, or on both the first and second surfaces 232 and 234. Any type or kind of anti-reflective coating may be utilized. In a representative embodiment, the composition of the anti-reflective coating 235 is tuned to the various ranges of wavelengths of the light emitted by the illumination source 205, such that any incident light on the second optical element 230 of a first pixel light source apparatus 200 from another, second pixel light source apparatus 200 of the partially-spherical dome (or shell) 110 is substantially not reflected. As a result, internal reflections from the pixel light source apparatuses 200 within the partially-spherical dome (or shell) 110 are greatly diminished and generally will not be reflected into the eye 265 of the subject 250.

For example, the design of each pixel light source apparatus 200 generally reduces or eliminates the reflecting of light from opposing surfaces of the interior of the partially-spherical dome (or shell) 110. In a representative embodiment, this may be accomplished by having the second optical element 230 include the first, anti-reflection coating 235 on one or both first and second surfaces 232 and 234. The second optical element 230 may contain a coating or inclusion to increase scattering of transmitted light.

In another, second representative embodiment, the second optical element 230 diffuses light, e.g., is substantially optically translucent, and may be comprised similarly or identically to the first optical element 220, as discussed below.

The side walls 210 and the rear or distal wall 240 of the pixel light source apparatus 200 may be comprised of any material, such as a metal, a polymer, a plastic, glass, etc., which is generally sufficiently opaque to the transmission of the various ranges of wavelengths of the light emitted by the illumination source 205, such that light emitted from an illumination source 205 does not pass through the side walls 210. In a representative embodiment, the side walls 210 and the rear or distal wall 240 are comprised of aluminum. In addition, as an option, the surfaces of the side walls 210 and the rear or distal wall 240 facing the first and second light chambers 270, 275 may also be polished or mirrored to be comparatively highly light reflective (such as for the first light chamber 270) or may be etched or roughened to be comparatively highly light diffusing or absorbing (such as for the second light chamber 275). The side walls 210 and the rear or distal wall 240 may have any selected thickness. In general, both the side walls 210 and the rear or distal wall 240 should be sufficiently thin to allow a sufficient number of pixel light source apparatuses 200 to be utilized in the partially-spherical dome (or shell) 110, but nonetheless have sufficient thickness to be structurally sound and robust during use of the system 100.

The illumination source 205 of the pixel light source apparatus 200 may comprise any type or kind of illumination or light emitting source. For example, the illumination source 205 may comprise one or more LEDs in a representative embodiment. Other types of lights or lamps may be utilized equivalently, including without limitation halogen lamps, fluorescent lamps, incandescent lamps, mercury and sodium vapor lamps, and so on. Optionally, the illumination source 205 may also include a lens or other transparent or translucent covering 295. For example, many commercially available LEDs include such a lens or other transparent or translucent covering 295. The illumination source 205 is generally located at or near the distal end 282, and may be coupled at or near the rear or distal wall 240. In other embodiments, the illumination source 205 may have other positions. For example and without limitation, a single or a plurality of illumination sources 205 may be utilized, with each illumination source 205 coupled to one or more side walls 210 at or near the distal end 282 of the pixel light source apparatus 200. Those having skill in the art will recognize additional variation, any and all of which are within the scope of the disclosure.

As another option, the pixel light source apparatus 200 may further comprise a third, diffusing optical element 285 arranged or disposed to be spaced-apart proximally from the illumination source 205 (between the illumination source 205 and the first, internal optical element 220) and coupled to the side walls 210 within the first, rear or distal light chamber 270. For example and without limitation, such a third optical element 285 may be included (as an option) when the illumination source 205 does not include a lens or other transparent or translucent covering 295. FIG. 10 illustrates the optional inclusion of both a third optical element 285 and a lens or other transparent or translucent covering 295, while no third optical element 285 is included in FIG. 14. When the third optical element 285 is included, the first, rear or distal light chamber 270, as illustrated in FIG. 10, is divided into two parts, first, rear or distal light chambers 270A and 270B, which are collectively referred to as a first, rear or distal light chamber 270.

The first, internal optical element 220 (and also the third optical element 285 and/or the lens or other transparent or translucent covering 295, and the second embodiment of the second optical element 230 mentioned above) of the pixel light source apparatus 200 may be any type of light diffusing structure and may comprise any substantially translucent material, including those discussed below for the first embodiment of the second optical element 230. In a representative embodiment, the first, internal optical element 220 (and also the third optical element 285 and/or the lens or other transparent or translucent covering 295) comprise a silicate glass or any type of plastic or polymer having a layer of glass spheres or beads arranged on one or both (proximal and distal) surfaces 222, 224. Also for example, in another representative embodiment, the first, internal optical element 220 (and also the third optical element 285 and/or the lens or other transparent or translucent covering 295 and the second embodiment of the second optical element 230) comprise a silicate glass or any type of plastic or polymer which is frosted or etched, or includes other surface structures (e.g., hemispheres) on one or both (proximal and distal) surfaces 222, 224, which provide light diffusion or other spreading. In other representative embodiments, the first, internal optical element 220 is translucent. In another representative embodiment, the first, internal optical element 220 is a transparent or translucent diverging lens. In addition, depending upon the selected embodiment, the first, internal optical element 220 may also provide color filtering (e.g., RGB).

The second optical element 230 of the pixel light source apparatus 200 also may be any type of light transmitting or diffusing structure and may comprise any substantially transparent or translucent material. As mentioned above, for a first embodiment of the second optical element 230, the second optical element 230 is substantially transparent, and for the second embodiment of the second optical element 230, the second optical element 230 is substantially translucent or otherwise diffusing. For example, the second optical element 230 may be comprised of any silicate glass or any type of plastic or polymer. Also for example, the second optical element 230 is comprised of any substantially optically transmissive material for various ranges of wavelengths of the light emitted by the illumination source 205, such as a borosilicate glass or polystyrene latex. Representative types of substantially transparent or translucent materials include, in addition to borosilicate glass (any silicate glass having at least 5% of boric oxide): soda-lime glass, a lead glass (including a lead-alkali glass), aluminosilicate glass (having aluminum oxide in its composition), ninety-six percent silica glass, and fused silica glass, for example and without limitation. As mentioned above, the first, internal optical element 220 and the second embodiment of the second optical element 230 may also be comprised of any of these materials, but then generally includes etching, frosting, embedded glass beads, or other surface structures which will be light diffusing.

The first, internal optical element 220 and the second optical element 230 of the pixel light source apparatus 200 may have any selected thickness. In general, both the first, internal optical element 220 and the second optical element 230 should be sufficiently thin to allow sufficient light to be emitted from the pixel light source apparatus 200, such as to cause saturation as discussed above, but nonetheless have sufficient thickness to be structurally sound and robust during use of the system 100.

As options, each pixel light source apparatus 200 further comprises several different internal coatings on the interior surfaces of the side walls 210 and the rear or distal wall 240, in addition to the first, anti-reflective (or comparatively highly reflective) coating 235 provided on the external surface 232 (or both surfaces 232, 234) of the second optical element 230. A second, reflective coating 215 of the pixel light source apparatus 200 is arranged or disposed to cover or coat the side walls 210 of the first, rear or distal light chamber 270, and may also be arranged or disposed to cover or coat the rear or distal wall 240 of the first, rear or distal light chamber 270. This second coating 215 is comparatively highly reflective for the various wavelength ranges of the light emitted by the illumination source 205. For example, in a representative embodiment, the second coating 215 may be barium sulfate or some other highly reflective coating, such as a silver or white coating or paint, a nano-structured reflective composition, a white or silver polymeric or plastic film or coating, or virtually anything white or silver (e.g., white paper or plastic) or otherwise reflective. Also for example, the first, anti-reflective coating 235 may include periodic layers of high-index materials (e.g., zinc sulfide or titanium dioxide) and low-index materials (e.g., magnesium fluoride or silicon dioxide) such that the reflection is tuned to the wavelengths emitted by the illumination source 205 (such as LEDs). Also other dielectric or metallic coatings known to those skilled in the art. As discussed above, when the side walls 210 and/or the rear or distal wall 240 have polished or mirrored internal surfaces forming the first, rear or distal light chamber 270, the second, reflective coating 215 may be omitted.

A third, non-reflective coating 225 of the pixel light source apparatus 200 is arranged or disposed to cover or coat the side walls 210 of the second, front or proximal light chamber 275. This third coating 225 is comparatively highly non-reflective, high absorbance for the various wavelength ranges of the light emitted by the illumination source 205. For example, in a representative embodiment, the third coating 225 may be flat black paint or flocking, carbon black, carbon nanotubes, a nano-structured light absorbing composition such as Vantablack™ or Acktar high absorbance black coatings such as VIS, SWIR and MWIR high absorbing coatings for stray light suppression, also for example. As discussed above, when the side walls 210 and/or the rear or distal wall 240 have roughened or otherwise non-reflective internal surfaces forming the second, front or proximal light chamber 275, the third coating 225 may be omitted.

Combination of such second and third coatings 215, 225 may also be utilized on different portions of the interior side walls 210 and the rear or distal wall 240 of the pixel light source apparatus 200. In addition, when included, the second and third coatings 215, 225 may have any selected thickness sufficient to be generally or substantially reflective and non-reflective, respectively.

Using these various second and third coatings 215, 225 (and/or internal surface treatments of the side walls 210 and the rear or distal wall 240), using the first, internal optical element 220 and the second optical element 230, and due to the generally elongated structure (longitudinally) of the pixel light source apparatus 200, the light generated by the illumination source 205 and leaving the pixel light source apparatus 200 through the second optical element 230 will be at least partially collimated, i.e., will be a beam having comparatively little divergence.

Referring to FIG. 7, for ease of reference, the longitudinal dimension (or cross-section) of the pixel light source apparatus 200 is illustrated as an "x" axis, and the transverse dimension (or cross-section) of the pixel light source apparatus 200 is illustrated as a "y" axis. As mentioned above, the pixel light source apparatus 200 is generally elongated in the longitudinal dimension as illustrated, and the pixel light source apparatus 200 longitudinal axis is oriented radially (illustrated using dashed lines in FIG. 7) in the partially-spherical dome (or shell) 110, such that a beam of light emitted from each pixel light source apparatus 200 will be provided to a convergent location (position or point) 290 of the partially-spherical dome (or shell) 110, as illustrated in FIG. 7. It should be noted that the convergent location (position or point) 290 is not located on or within the partially-spherical dome (or shell) 110, but is spaced-apart from the partially-spherical dome (or shell) 110 and located or positioned based upon the orientations of the plurality of pixel light source apparatuses 200, so the convergent location (position or point) 290 may be within the concave region bounded by the partially-spherical dome (or shell) 110 or may be external to the partially-spherical dome (or shell) 110. While a singular convergent location 290 is generally utilized in the representative system 100, those having skill in the art will recognized that multiple convergent locations 290 could also be implemented, such as a tight grouping of convergent locations 290 positioned similarly to the singular convergent location 290 illustrated in FIGS. 4 and 7, and any and all such variations are within the scope of the disclosure.

As mentioned above, for testing, a subject 250 is positioned or aligned in front of the partially-spherical dome (or shell) 110, such that the eye 265 of the subject 250 is at this convergent location 290, with the individual subject 250 generally looking at the center 160 of the partially-spherical dome (or shell) 110. The relative positions of the partially-spherical dome (or shell) 110 and the subject 250 may be arranged, moved or otherwise varied to provide this visual alignment. This alignment allows the image of each pixel light source apparatus 200 to be focused by the optics of the eye 265 of the subject 250 and stimulate a corresponding part of the retina of the eye 265 of the subject 250. As each pixel light source apparatus 200 may be selectively and independently energized, the plurality of the pixel light source apparatuses 200 may produce any illuminated pattern on the interior surface of the partially-spherical dome (or shell) 110. The pattern may illuminate any portion of the partially-spherical dome (or shell) 110, thereby allowing the evaluation of the entire retina. Each pixel light source apparatus 200 may thereby correspond to a section of a retina. This allows the user to probe any arbitrary section of the retina by providing a visual stimulus to a section of the retina by illuminating the associated pixel light source apparatuses 200 of the partially-spherical dome (or shell) 110.

While the pixel light source apparatus 200 is generally elongated and/or tubular, each pixel light source apparatus 200 may have virtually any shape and size, with pixel light source apparatuses 200A, 200B, 200C, and 200D providing examples. For example and without limitation, a pixel light source apparatus 200 may be trapezoidal in the longitudinal dimension (or cross-section), such as illustrated in FIG. 10 for the representative first and second pixel light source apparatus 200A, 200B, or may be rectangular in longitudinal dimension (or cross-section), such as illustrated in FIG. 14 for the representative third and fourth pixel light source apparatus 200C, 200D.

In addition, a pixel light source apparatus 200 may have any polygonal, circular, elliptical or other shape in the transverse dimension (or cross-section). For example and without limitation, a pixel light source apparatus 200 may be square or rectangular in transverse dimension (or cross-section), such as illustrated in FIG. 8 for the representative first pixel light source apparatus 200A; or a pixel light source apparatus 200 may be hexagonal in transverse dimension (or cross-section), such as illustrated in FIG. 9 for the representative second pixel light source apparatus 200B and as illustrated in FIG. 12 for the representative third pixel light source apparatus 200C; or a pixel light source apparatus 200 may be triangular in transverse dimension (or cross-section), such as illustrated in FIG. 13 for the representative fourth pixel light source apparatus 200D. For example, the polygonal transverse dimension (or cross-section) of each pixel light source apparatus 200 may be of a triangular, square, rectangulary pentagonal, hexagonal, septagonal, octagonal, or another polygonal configuration, or the pixel light source apparatus 200 may have a circular, ovoid, elliptical, etc. transverse dimension (or cross-section). The transverse dimensions (or cross-sections) of the pixel light source apparatuses 200 may not all be of the same shape. For example, some of the transverse dimensions (or cross-sections) of the pixel light source apparatuses 200 may be pentagonal and some may be hexagonal.

Stated another way, the pixel light source apparatuses 200 which are trapezoidal in the longitudinal dimension (or cross-section) may also be considered a conical frustum, or a pyramidal frustum, or a hexagonal frustum, or a triangular frustum, or a pentagonal frustum, a square frustum, or an octagonal frustum, and so on, as illustrated in FIGS. 8 and 9. When arranged in a partially-spherical dome (or shell) 110 and viewed by a properly aligned subject 250, such frustum embodiments of pixel light source apparatuses 200 create a "viewing frustum" for each pixel. A particular advantage of this configuration is that eye 265 of the subject 250 views only the surfaces of the most proximal portions of the pixel light source apparatuses 200, such as only the second optical element 230, and not the side walls 210, including the side walls 210 having the third, non-reflective coating 225.

The pixel light source apparatuses 200 are disposed or arranged to form a partially-spherical dome (or shell) 110 for a representative system 100 embodiment. Several variations of this arrangement of the pixel light source apparatuses 200 to form a partially-spherical dome (or shell) 110 for a representative system 100 embodiment are illustrated and any and all variations are within the scope of this disclosure. The individual pixel light source apparatuses 200 may each have a transverse (or cross-sectional) shape such that the pixel light source apparatuses 200 can be arranged with the front or proximal ends 280 set adjacent to one another, either abutting (as illustrated in FIG. 7) or adjacent but spaced-apart (as illustrated in FIG. 11), and arranged to form a partially-spherical dome (or shell) 110, or to tile a surface of arbitrary curvature, such as any other surface that may be similar to Buckyball geometry. The partially-spherical dome (or shell) 110 may be comprised of a plurality of triangular (transversely) pixel light source apparatuses 200, or a plurality of hexagonal (transversely) pixel light source apparatuses 200, or a plurality of pentagonal (transversely) pixel light source apparatuses 200, or a plurality of square (transversely) pixel light source apparatuses 200, or a plurality of rectangular (transversely) pixel light source apparatuses 200, or it may be comprised of a combination of pixel light source apparatuses 200 of various polygonal, circular or elliptical transverse dimension or cross-sections; for example and without limitation, a plurality of hexagonal (transversely) pixel light source apparatuses 200 combined with a plurality of pentagonal (transversely) pixel light source apparatuses 200. The partially-spherical dome (or shell) 110 may also be considered to form a partially-spherical surface in the interior, concave side 108, comprised of the front or proximal ends 280 of the various pixel light source apparatuses 200.

For example, two such available arrangements of the pixel light source apparatuses 200 are illustrated in FIG. 7, which may be any of the various pixel light source apparatuses 200, e.g., 200A, 200B. As illustrated in FIG. 7, the pixel light source apparatuses 200 are trapezoidal in the longitudinal dimension. In addition, the pixel light source apparatuses $200_1$ are abutting each other in the partially-spherical dome (or shell) 110. Other pixel light source apparatuses $200_2$, however, are spaced-apart from each other in the partially-spherical dome (or shell) 110. Other pixel light source apparatuses $200_3$, however, share one or more side walls 210 with each other, illustrated as side walls 210A, with a single side wall 210A being common to more than one pixel light source apparatus $200_3$. The one or more side walls, whether shared or separate, separate each illumination source 205 in a pixel light source apparatus 200 from its neighbors. Any and all of these variations are within the scope of the disclosure.

Also for example, two additional available arrangements of the pixel light source apparatuses 200 are illustrated in FIG. 11, which may be any of the various pixel light source apparatuses 200, e.g., 200C, 200D. As illustrated in FIG. 11, the pixel light source apparatuses 200 are rectangular in the longitudinal dimension. In addition, the front or proximal ends 280 of pixel light source apparatuses $200_4$ are abutting each other in the partially-spherical dome (or shell) 110. The front or proximal ends 280 of other pixel light source apparatuses $200_5$, however, are spaced-apart from each other in the partially-spherical dome (or shell) 110. Any and all of these variations are also within the scope of the disclosure.

Figure 15:
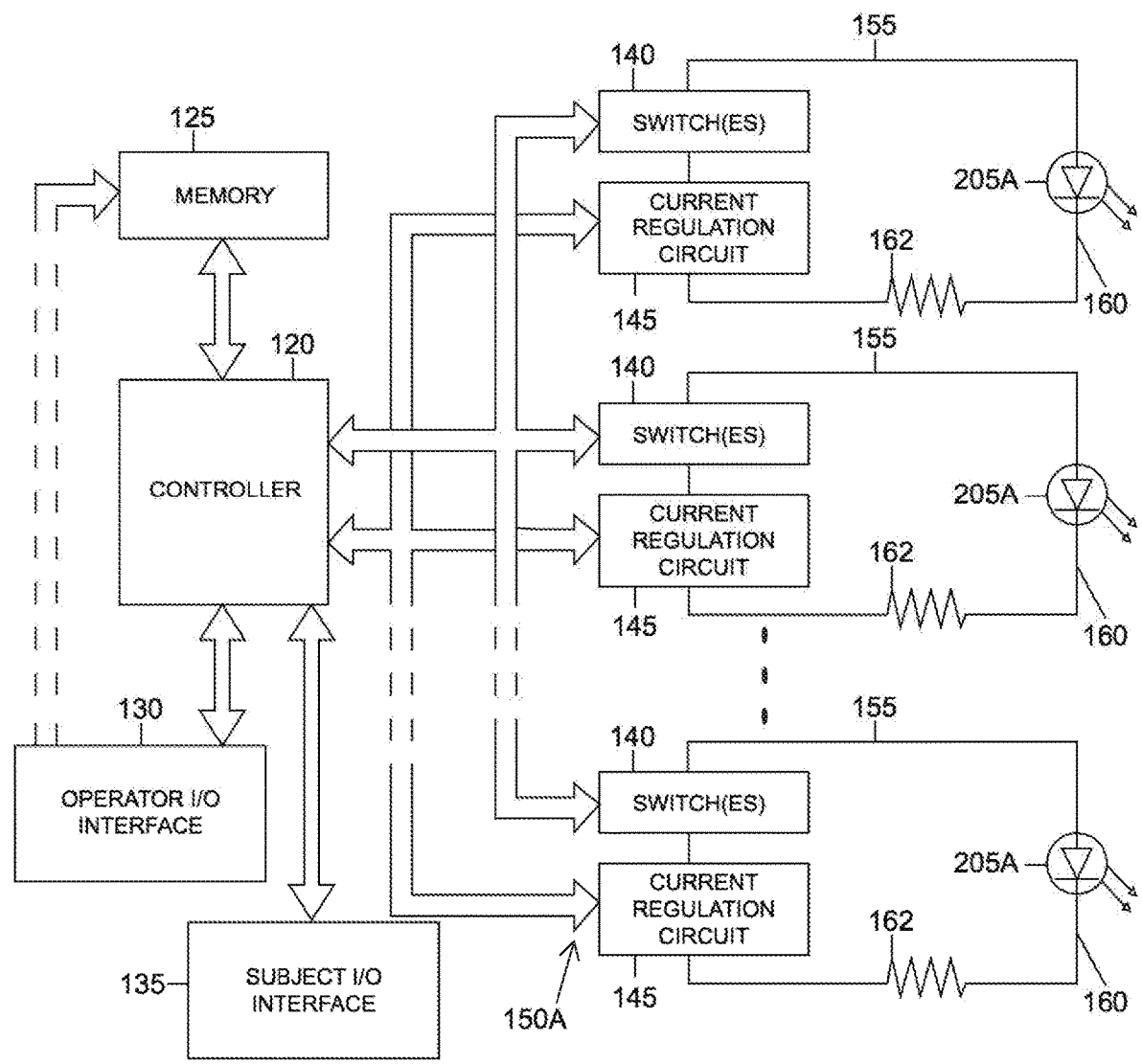
FIG. 15 is a block and circuit diagram illustrating a first representative embodiment of control and drive circuitry for a representative system embodiment.
Figure 16:
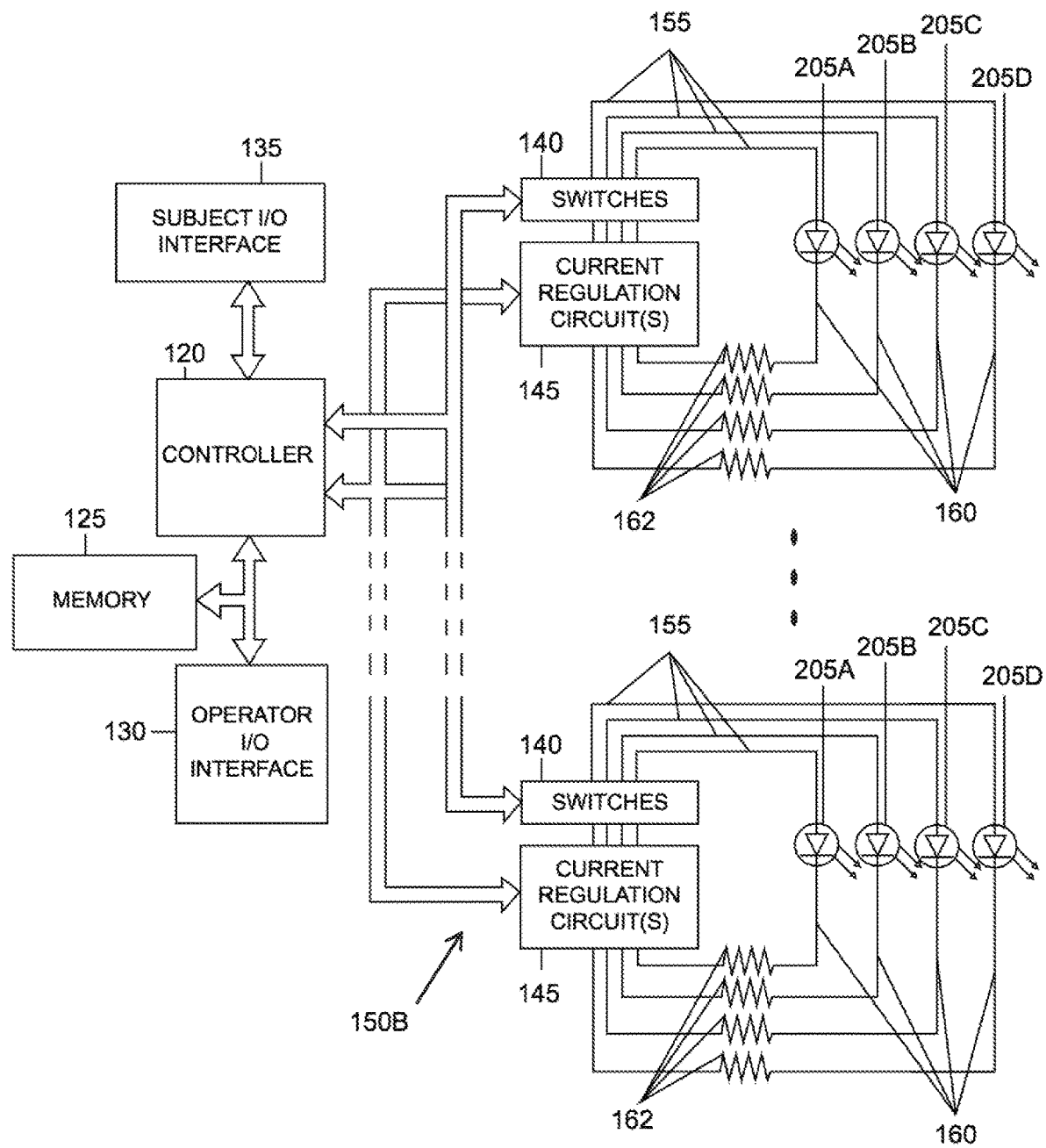
FIG. 16 is a block and circuit diagram illustrating a second representative embodiment of control and drive circuitry for a representative system embodiment.

FIG. 15 is a block and circuit diagram illustrating a first representative embodiment of control and drive circuitry 150A for a representative system 100 embodiment. FIG. 16 is a block and circuit diagram illustrating a second representative embodiment of control and drive circuitry 150B for a representative system 100 embodiment. The first and second representative embodiments of control and drive circuitry 150A, 150B are merely provided for completeness as examples of typical control and drive circuitry which may be utilized in a system 100, with the pixel light source apparatuses 200 in a partially-spherical dome (or shell) 110, and should not be regarded as limiting in any way.

As discussed above, each pixel light source apparatus 200 may have one or more illumination sources 205. As illustrated in FIG. 15, the first embodiment of control and drive circuitry 150A is for one or more pixel light source apparatuses 200 which each utilize a single LED as an illumination source 205, illustrated as illumination source 205A in FIG. 15, such as an LED to emit white light, for example and without limitation. As illustrated in FIG. 16, the second embodiment of control and drive circuitry 150B is for one or more pixel light source apparatuses 200 in which at least some pixel light source apparatuses 200 each utilize a plurality of LEDs as illumination sources 205, illustrated as illumination sources 205A, 205B, 205C, and 205D in FIG. 16, such as LEDs to emit white, red, green, and/or blue light, for example and without limitation. In addition, any combination of these first and second embodiments of control and drive circuitry 150A, 150B is also within the scope of the disclosure.

As illustrated in FIGS. 15 and 16, the first and second representative embodiments of control and drive circuitry 150A, 150B each comprise one or more switches 140, one or more current regulation circuits 145, a controller (or processor) 120, a memory circuit 125, an operator input/output ("I/O") interface 130 (typically coupleable to receive commands and/or data from the operator control panel 105), and a subject I/O interface 135 (typically coupleable to receive commands and/or data from the subject interface (or panel) 115). As an option, a computing system 195 may also be coupled to a controller (or processor) 120 (not separately illustrated).

Also as illustrated in FIGS. 15 and 16, each illumination source (LED) 205 is coupled to a switch 140, such as a transistor, and typically coupled through a resistor 162 to a current regulation circuit 145, which may provide a constant current or may provide a variable current, such as for dimming. Such current regulation circuits and other control and drive circuitry are well known in the electronic arts, and any current regulation circuit 145 may be utilized, such as any of the drive and/or current regulation circuits disclosed, for example and without limitation, in U.S. Pat. Nos. 7,880,400; 8,970,133; 8,704,462; 8,749,175; each of which is hereby incorporated herein by reference in its entirety with the same full force and effect as if set forth in its entirety herein. Other power supplies and corresponding circuits may also be included (not separately illustrated).

The controller (or processor) 120, in conjunction with any data stored in the memory 125, together with any commands and/or data received through the operator I/O interface 130 from the operator control panel 105, will issue commands and or other signals (e.g., on/off signals to switches 140, current level commands or settings to the current regulation circuits 145, etc.), to implement any of the ERG and other protocols discussed above, such as to flash or dim one or more of the illumination sources 205, in any combination and/or permutation. As mentioned above, the illumination source 205 may be an array of LEDs each emitting a different wavelength of light such that under the control of the controller (or processor) 120, a combination of LEDs can be activated to produce a mixture of wavelengths of light emitted from the front 280 of the pixel light source apparatus 200. The mixture can be designed to produce the sensation of "white" light to an observer, or to produce the sensation of different colors or hues (e.g., red, green, blue).

A controller (or processor) 120 and a non-transient computer-readable memory storing instructions (e.g., memory 125) may be provided. The controller (or processor) 120 may execute instructions from the memory 125, thereby causing one or a plurality of the illumination sources 205 or pixel light source apparatuses 200 to become illuminated. An operator I/O interface 130 configured to receive an input from the operator control panel 105 allows a user to determine a frequency (i.e., temporal frequency), intensity, and location of illumination of the illumination sources 205 or pixel light source apparatuses 200. The user may cause the illumination of a pattern that includes illuminating a first subset of the illumination sources 205 or pixel light source apparatuses 200, then illuminating a second subset of illumination sources 205 or pixel light source apparatuses 200, for example and without limitation. Pixel light source apparatuses 200 chosen for illumination would be selected via an operator control panel 105 or a computing system 195, and on user command the stimulus (typically a brief flash, or series of flashes, of white or colored light) may be delivered by the selected pixel light source apparatuses 200.

Numerous advantages of the representative embodiments are readily apparent. Also for example, under the operation and control of the controller (or processor) 120, each of the pixel light source apparatuses 200 may be illuminated or turned on individually or in any combination, and the luminance or intensity of each pixel light source apparatus 200 may also be individually controllable. This flexibility in being able to light different portions of the partially-spherical dome (or shell) 110, and in being able to have varying degrees of illumination allows the user to probe any arbitrary section of the retina, by providing a visual stimulus to that part of the retina by illuminating the corresponding pixel light source apparatuses 200 of the partially-spherical dome (or shell) 110, thereby ascertaining a measure of local health. This system 100 therefore adds a significant new dimension to ERG testing, namely, spatial selectivity. Also for example, the controller (or processor) 120 also be programmed to present the kind of stimulus used in the multi-focal ERG test, thereby expanding that test from evaluating the central retina only to evaluating the entire retina. Also for example, the controller (or processor) 120 also be programmed to present the kind of stimulus used in any of the various protocols mentioned above.

Pixel light source apparatuses 200 chosen for illumination are selected via a commands and/or data from the operator control panel 105, and on user command the visual stimulus would be delivered by the selected pixel light source apparatuses 200, and the ERG response recorded using standard ERG recording techniques. The stimulus may typically comprise a brief flash, or series of flashes, of white or colored light, although a constant light could also be used, alone or in combination with full-field or pattern flashes.

Also advantageously, the representative system 100 can also be used to perform novel psychophysical tests, such as perimetry and contrast sensitivity, by using the stimulus in conjunction with a subject-response system, as is routinely done in Humphrey Visual Field testing. Using the representative system 100 in this manner would greatly increase the utility of these common clinical tests by extending the area of the retina that is evaluated all the way to the edges of the visual field. Current perimetry and contrast sensitivity testing only evaluate the central retina, such as due to the limitations on the design of the stimulus source. The representative system 100 overcomes these limitations and allows stimuli under individual control to be presented to any part of the retina.

One advantage of the representative system 100 is that it could be used to measure the limits of the visual field using an objective and reliable electrophysiological measure (e.g., an ERG response to a local stimulus) as opposed to relying on the voluntary response of the subject (e.g., a button push). In contrast, prior art psychophysical (i.e., subject-response types of tests) are generally (and notoriously) unreliable due to subject non-compliance and inconsistency, for example, and further because these types of tests involve other aspects of the person's physiology beyond the visual pathway.

Also advantageously, the representative system 100 is also able to probe the entire retina using any arbitrary user-defined set of stimulus areas. This clinical test could be used, for example, to screen for local dysfunction by "scanning" the retina section by section, to test for dysfunction in areas where structural or imaging tests suggest a potential problem, or to evaluate functional improvement where a local therapeutic intervention has been introduced (gene therapy, cryotherapy, photocoagulation, etc.). The benefit of localized measurements versus traditional full-field ERG is a clinically significant increase in sensitivity to localized changes in function or health state of the retina.

Yet another advantage, the representative system 100 has the ability to test arbitrary areas of the retina, which would be in addition to the ability to perform all tests that current full-field stimulus sources are used for (full-field homogeneous flashes of white or colored light, ramp or step stimuli, paired-flash sequences, bleaching background lights, etc.). This would give the clinician or researcher unparalleled flexibility in designing testing protocols or sequences of protocols to diagnose and monitor retinal disease.

This representative system 100 overcomes the limitation of flat (CRT or LED computer monitors) ERG stimulus sources by filling the entire visual field. By creating a three-dimensional dome-shaped stimulus source that surrounds the eye, there are pixels in the stimulus that correspond with every part of the anatomical retina. The focal ERG approach described here overcomes all of these limitations in a single piece of hardware, namely, the representative system 100.

An additional problem solved by this approach is that using LEDs as a light source can create a stimulus of higher luminance than is possible with current flat-panel displays. This allows greater flexibility in designing the stimulus protocol for evaluating different aspects of retinal function.

Figure 17A:
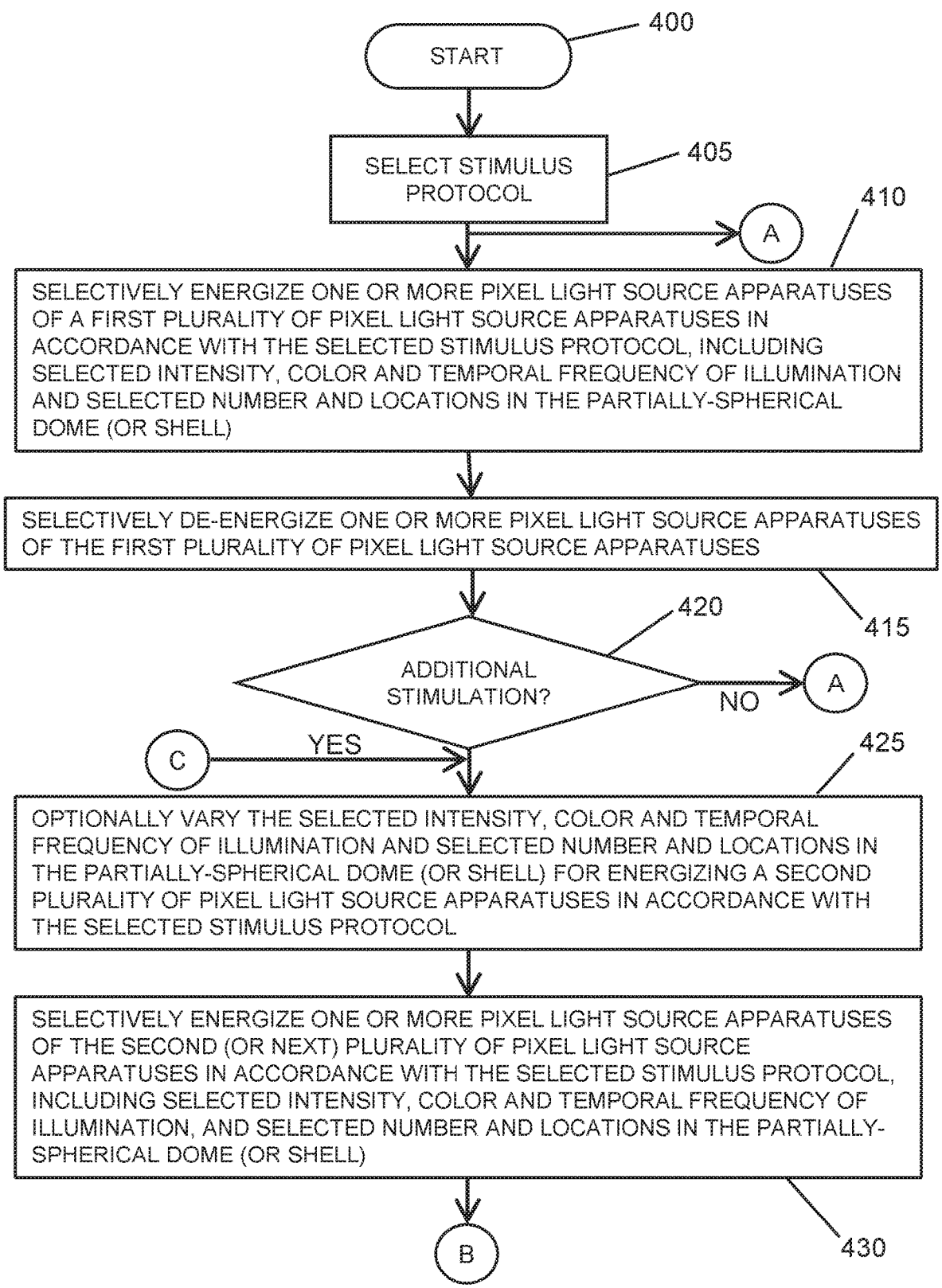
FIGS. 17A and 17B (collectively "FIG. 17) is a flow diagram illustrating a representative method embodiment.
Figure 17B:
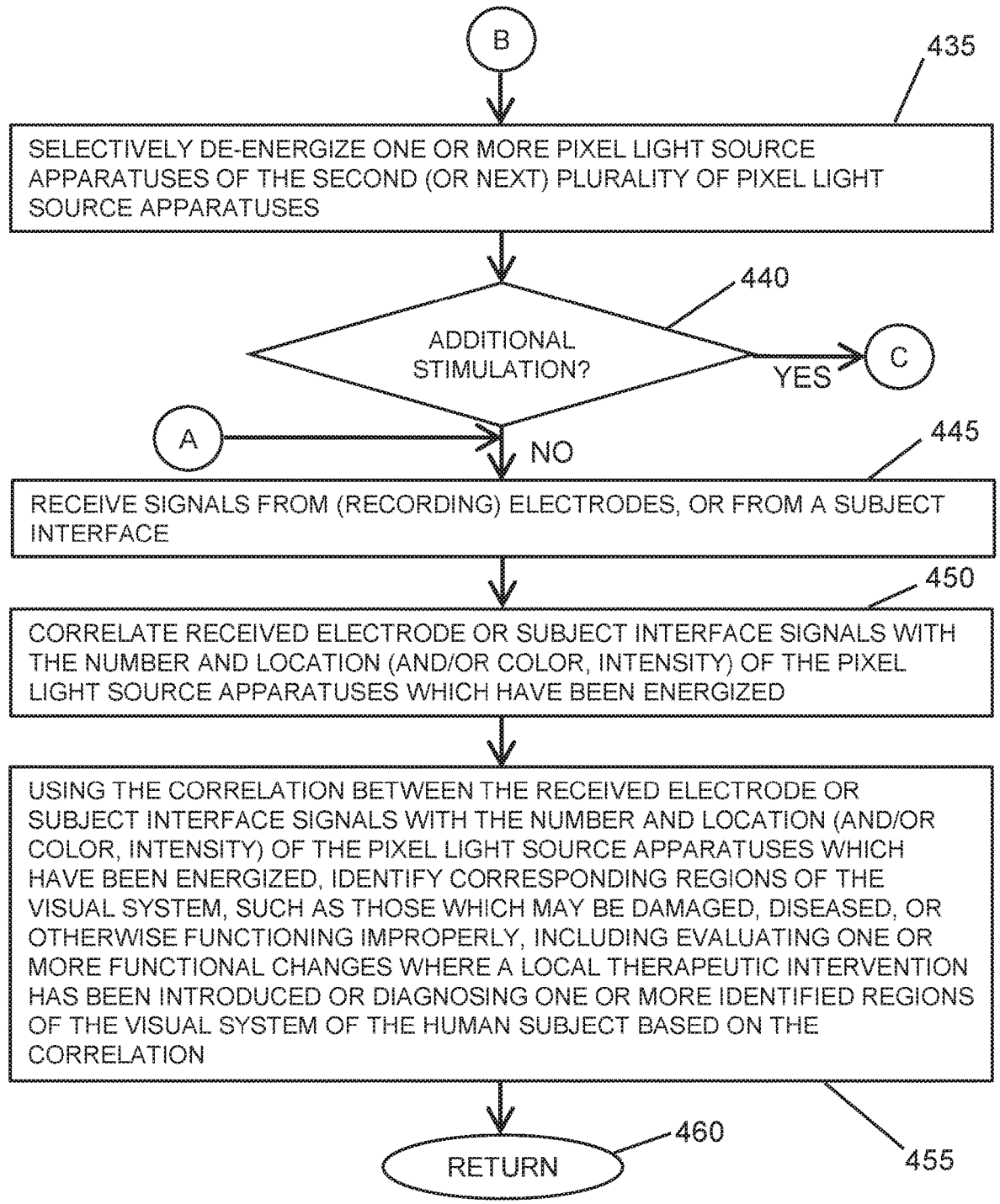

A representative system 100 also provides for greater sensitivity in testing visual pathway function. Importantly, the ability to saturate the visual pathway provided by the representative system 100 allows for normalization of responses across subjects, as responses to stimuli of lower strength are normalized to a maximal (saturated) response for each subject. This compensates for wide differences in ERG amplitude that are not related to the health of the retina, but to other factors such as the type or style of a recording electrode or placement of a reference electrode. In the prior art, if the stimulus source is not capable of saturating the visual pathway, this type of normalization cannot be accomplished, and the sensitivity of any given test is substantially reduced, as the variation in response amplitude that is considered "healthy" goes up substantially FIG. 17 is a flow diagram illustrating a representative method embodiment, and provides a useful summary. Beginning with start step 400, a stimulus protocol is selected, step 405, such as by user entry or through the controller (or processor) 120 accessing the memory 125. The stimulus protocol will generally specify the number (quantity) and location of the plurality of pixel light source apparatuses 200 being energized or de-energized, the modulation of the brightness or intensity of any of the plurality of pixel light source apparatuses 200, the color of any of the plurality of pixel light source apparatuses 200, and the modulation of any temporal frequency of such energizing and de-energizing, such as dimming, on, off, flashing, bursting, etc., for example and without limitation.

The controller (or processor) 120 then generates commands or other signals to the various switches 140 and current regulation circuits 145 to selectively energize one or more pixel light source apparatuses 200 of a first plurality of pixel light source apparatuses 200 in accordance with the selected stimulus protocol, step 410. In a representative embodiment, as part of the selected stimulus protocol, each of the pixel light source apparatuses 200 of the first plurality of pixel light source apparatuses 200 has a selected intensity, color and (temporal) frequency of illumination and a selected location in the partially-spherical dome (or shell) 110. In accordance with the selected stimulus protocol, the controller (or processor) 120 then generates commands or other signals to the various switches 140 and current regulation circuits 145 to selectively de-energize one or more pixel light source apparatuses 200 of the first plurality of pixel light source apparatuses 200, step 415.

When additional stimulation is to occur in the selected stimulus protocol, step 420, in accordance with the selected stimulus protocol, for any of the various to energizing and de-energizing steps, as illustrated for step 425, the number (quantity), color and location of the plurality of pixel light source apparatuses 200 being energized or de-energized, the modulation of the brightness or intensity of any of the plurality of pixel light source apparatuses 200, and the modulation of any temporal frequency of such energizing and de-energizing, is generally varied, as an option. The controller (or processor) 120 generates commands or other signals to the various switches 140 and current regulation circuits 145 to selectively energize one or more pixel light source apparatuses 200 of a second (or next) plurality of pixel light source apparatuses 200 in accordance with the selected stimulus protocol, step 430. In a representative embodiment, as part of the selected stimulus protocol, each of the pixel light source apparatuses 200 of the second (or next) plurality of pixel light source apparatuses 200 also has a selected intensity and temporal frequency of illumination, a selected color, and a selected location in the partially-spherical dome (or shell) 110. In accordance with the selected stimulus protocol, the controller (or processor) 120 then generates commands or other signals to the various switches 140 and current regulation circuits 145 to selectively de-energize one or more pixel light source apparatuses 200 of the second (or next) plurality of pixel light source apparatuses 200, step 435. When additional stimulation is to occur in the selected stimulus protocol, step 440, the method returns to step 425 and iterates, performing steps 425, 430 and 435, in accordance with the selected stimulus protocol, until completion.

Concurrently with steps 410 through 440, a recording device, such as a stimulus response recorder 260, is receiving signals from one or more electrodes 255, step 445, or a response is received from a subject interface 115 (e.g., when a subject presses a button, for example), which continues until terminated in accordance with the selected stimulus protocol. Following step 445, in step 450, the received electrode 255 signals are correlated with the number and location of the pixel light source apparatuses 200 which have been energized in steps 410, 415, 430 and 435, typically using a computing system 195. As mentioned above, the various locations of the plurality of pixel light source apparatuses 200 within the partially-spherical dome (or shell) 110 correspond to locations in a retina of an eye 265 of the subject 250. This allows probing of any arbitrary or selected part of the retina. Using the correlation between the received electrode 255 signals with the number and location of the pixel light source apparatuses 200 which have been energized, in step 455, the method identifies corresponding regions of the visual system, such as those which may be damaged, diseased, or otherwise functioning improperly, including evaluating one or more functional changes where a local therapeutic intervention has been introduced or diagnosing one or more identified regions of the visual system of the human subject based on the correlation, also typically using the computing system 195. Following step 455, the method may end return step 460.

For example, in addition to the use of recording electrodes 255, for step 445, the received signals may be from a behavioral response of the subject such as pressing a button provided as or on a subject interface 115. In addition, for step 445, the received signals may be from the one or more electrodes 255 simultaneously with a behavioral response of the subject such as pressing a button provided as or on a subject interface 115.

As used herein, a "controller" (or "processor") 120 and/or processor 320 may be any type of controller or processor, and may be embodied as one or more controller(s) 120 or processor(s) 320, configured, designed, programmed or otherwise adapted to perform the functionality discussed herein. As the term controller or processor is used herein, a controller 120 or processor 320 may include use of a single integrated circuit ("IC"), or may include use of a plurality of integrated circuits or other components connected, arranged or grouped together, such as controllers, microprocessors, digital signal processors ("DSPs"), array processors, graphics or image processors, parallel processors, multiple core processors, custom ICs, application specific integrated circuits ("ASICs"), field programmable gate arrays ("FPGAs"), adaptive computing ICs, associated memory (such as RAM, DRAM and ROM), and other ICs and components, whether analog or digital. As a consequence, as used herein, the term processor or controller should be understood to equivalently mean and include a single IC, or arrangement of custom ICs, ASICs, processors, microprocessors, controllers, FPGAs, adaptive computing ICs, or some other grouping of integrated circuits which perform the functions discussed herein, with associated memory, such as microprocessor memory or additional RAM, DRAM, SDRAM, SRAM, MRAM, ROM, FLASH, EPROM or $E^2$PROM. A controller 120 or processor 320, with associated memory, may be adapted or configured (via programming, FPGA interconnection, or hard-wiring) to perform the methodology of the invention, as discussed herein. For example, the methodology may be programmed and stored, in a controller 120 or processor 320 with its associated memory (and/or memory 125 or memory 325) and other equivalent components, as a set of program instructions or other code (or equivalent configuration or other program) for subsequent execution when the controller 120 or processor 320 is operative (i.e., powered on and functioning). Equivalently, when the controller 120 or processor 320 may implemented in whole or part as FPGAs, custom ICs and/or ASICs, the FPGAs, custom ICs or ASICs also may be designed, configured and/or hard-wired to implement the methodology of the invention. For example, the controller 120 or processor 320 may be implemented as an arrangement of analog and/or digital circuits, controllers, microprocessors, DSPs and/or ASICs, collectively referred to as a "processor" or "controller", which are respectively hard-wired, programmed, designed, adapted or configured to implement the methodology of the invention, including possibly in conjunction with a memory 125 or memory 325.

The memory 125 and/or memory 325, which may include a data repository (or database), may be embodied in any number of forms, including within any computer or other machine-readable data storage medium, memory device or other storage or communication device for storage or communication of information, currently known or which becomes available in the future, including, but not limited to, a memory integrated circuit ("IC"), or memory portion of an integrated circuit (such as the resident memory within a controller 120 or processor 320 or processor IC), whether volatile or non-volatile, whether removable or non-removable, including without limitation RAM, FLASH, DRAM, SDRAM, SRAM, MRAM, FeRAM, ROM, EPROM or $E^2$PROM, or any other form of memory device, such as a magnetic hard drive, an optical drive, a magnetic disk or tape drive, a hard disk drive, other machine-readable storage or memory media such as a floppy disk, a CDROM, a CD-RW, a digital versatile disk (DVD) or other optical memory, or any other type of memory, storage medium, or data storage apparatus or circuit, which is known or which becomes known, depending upon the selected embodiment. The memory 125 and memory 325 may be adapted to store various look up tables, parameters, coefficients, other information and data, programs or instructions (of the software of the present invention), and other types of tables such as database tables.

As indicated above, the controller 120 or processor 320 is hard-wired or programmed, using software and data structures of the invention, for example, to perform the methodology of the present invention. As a consequence, the system and method of the present invention may be embodied as software which provides such programming or other instructions, such as a set of instructions and/or metadata embodied within a non-transitory computer readable medium, discussed above. In addition, metadata may also be utilized to define the various data structures of a look up table or a database. Such software may be in the form of source or object code, by way of example and without limitation. Source code further may be compiled into some form of instructions or object code (including assembly language instructions or configuration information). The software, source code or metadata of the present invention may be embodied as any type of code, such as C, C++, Matlab, SystemC, LISA, XML, Java, Brew, SQL and its variations (e.g., SQL 99 or proprietary versions of SQL), DB2, Oracle, or any other type of programming language which performs the functionality discussed herein, including various hardware definition or hardware modeling languages (e.g., Verilog, VHDL, RTL) and resulting database files (e.g., GDSII). As a consequence, a "construct", "program construct", "software construct" or "software", as used equivalently herein, means and refers to any programming language, of any kind, with any syntax or signatures, which provides or can be interpreted to provide the associated functionality or methodology specified (when instantiated or loaded into a processor or computer and executed, including the controller 120 or processor 320, for example).

The software, metadata, or other source code of the present invention and any resulting bit file (object code, database, or look up table) may be embodied within any tangible, non-transitory storage medium, such as any of the computer or other machine-readable data storage media, as computer-readable instructions, data structures, program modules or other data, such as discussed above with respect to the memory 125 and/or memory 325, e.g., a floppy disk, a CDROM, a CD-RW, a DVD, a magnetic hard drive, an optical drive, or any other type of data storage apparatus or medium, as mentioned above.

The network interface 315 and the various operator and subject I/O interface circuit(s) 130, 135 are utilized for appropriate connection to a relevant channel, network or bus; for example, the network interface 315 and the operator and subject I/O interface circuit(s) 130, 135 may provide impedance matching, drivers and other functions for a wireline interface, may provide demodulation and analog to digital conversion for a wireless interface, and may provide a physical interface, respectively, for the computing system 195 (with processor 320 and memory 325) and for the controller (or processor) 120 and/or memory 125, with other devices. In general, the network interface 315 and the operator and subject I/O interface circuit(s) 130, 135 are used to receive and transmit data, depending upon the selected embodiment, such as program instructions, parameters, configuration information, control messages, data and other pertinent information.

The network interface 315 and the operator and subject I/O interface circuit(s) 130, 135 may be implemented as known or may become known in the art, to provide data communication between the processor 320 or controller 120, respectively, and any type of network or external device, such as wireless, optical, or wireline, and using any applicable standard (e.g., one of the various PCI, USB, RJ 45, Ethernet (Fast Ethernet, Gigabit Ethernet, 300ase-TX, 300ase-FX, etc.), IEEE 802.11, WCDMA, WiFi, GSM, GPRS, EDGE, 3G and the other standards and systems mentioned above, for example and without limitation), and may include impedance matching capability, voltage translation for a low voltage processor to interface with a higher voltage control bus, wireline or wireless transceivers, and various switching mechanisms (e.g., transistors) to turn various lines or connectors on or off in response to signaling from the processor 320 or controller 120, respectively. In addition, the network interface 315 and the operator and subject I/O interface circuit(s) 130, 135 may also be configured and/or adapted to receive and/or transmit signals externally to the computing system 195 and/or system 100, respectively, such as through hard-wiring or RF or infrared signaling, for example, to receive information in real-time for output on a display, for example. The network interface 315 and the operator and subject I/O interface circuit(s) 130, 135 may provide connection to any type of bus or network structure or medium, using any selected architecture. By way of example and without limitation, such architectures include Industry Standard Architecture (ISA) bus, Enhanced ISA (EISA) bus, Micro Channel Architecture (MCA) bus, Peripheral Component Interconnect (PCI) bus, SAN bus, or any other communication or signaling medium, such as Ethernet, ISDN, T1, satellite, wireless, and so on.

The present disclosure is to be considered as an exemplification of the principles of the invention and is not intended to limit the invention to the specific embodiments illustrated. In this respect, it is to be understood that the invention is not limited in its application to the details of construction and to the arrangements of components set forth above and below, illustrated in the drawings, or as described in the examples. Systems, methods and apparatuses consistent with the present invention are capable of other embodiments and of being practiced and carried out in various ways.

Although the invention has been described with respect to specific embodiments thereof, these embodiments are merely illustrative and not restrictive of the invention. In the description herein, numerous specific details are provided, such as examples of electronic components, electronic and structural connections, materials, and structural variations, to provide a thorough understanding of embodiments of the present invention. One skilled in the relevant art will recognize, however, that an embodiment of the invention can be practiced without one or more of the specific details, or with other apparatus, systems, assemblies, components, materials, parts, etc. In other instances, well-known structures, materials, or operations are not specifically shown or described in detail to avoid obscuring aspects of embodiments of the present invention. In addition, the various Figures are not drawn to scale and should not be regarded as limiting.

Reference throughout this specification to "one embodiment", "an embodiment", or a specific "embodiment" means that a particular feature, structure, or characteristic described in connection with the embodiment is included in at least one embodiment of the present invention and not necessarily in all embodiments, and further, are not necessarily referring to the same embodiment. Furthermore, the particular features, structures, or characteristics of any specific embodiment of the present invention may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention.

It will also be appreciated that one or more of the elements depicted in the Figures can also be implemented in a more separate or integrated manner, or even removed or rendered inoperable in certain cases, as may be useful in accordance with a particular application. Integrally formed combinations of components are also within the scope of the invention, particularly for embodiments in which a separation or combination of discrete components is unclear or indiscernible. In addition, use of the term "coupled" herein, including in its various forms such as "coupling" or "couplable", means and includes any direct or indirect electrical, structural or magnetic coupling, connection or attachment, or adaptation or capability for such a direct or indirect electrical, structural or magnetic coupling, connection or attachment, including integrally formed components and components which are coupled via or through another component.

With respect to signals, we refer herein to parameters that "represent" a given metric or are "representative" of a given metric, where a metric is a measure of a state of at least part of the regulator or its inputs or outputs. A parameter is considered to represent a metric if it is related to the metric directly enough that regulating the parameter will satisfactorily regulate the metric. A parameter may be considered to be an acceptable representation of a metric if it represents a multiple or fraction of the metric.

Furthermore, any signal arrows in the drawings/Figures should be considered only exemplary, and not limiting, unless otherwise specifically noted. Combinations of components of steps will also be considered within the scope of the present invention, particularly where the ability to separate or combine is unclear or foreseeable. The disjunctive term "or", as used herein and throughout the claims that follow, is generally intended to mean "and/or", having both conjunctive and disjunctive meanings (and is not confined to an "exclusive or" meaning), unless otherwise indicated. As used in the description herein and throughout the claims that follow, "a", "an", and "the" include plural references unless the context clearly dictates otherwise. Also as used in the description herein and throughout the claims that follow, the meaning of "in" includes "in" and "on" unless the context clearly dictates otherwise.

The foregoing description of illustrated embodiments of the present invention, including what is described in the summary or in the abstract, is not intended to be exhaustive or to limit the invention to the precise forms disclosed herein. From the foregoing, it will be observed that numerous variations, modifications and substitutions are intended and may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

It is claimed:

1. A pixel light source apparatus for a stimulus source for visual pathway testing, the pixel light source apparatus comprising:
   at least one side wall, the at least one side wall elongated in a longitudinal dimension along a longitudinal axis and optically opaque;
   a rear wall coupled to the at least one side wall, the rear wall orthogonal to the longitudinal axis and forming a distal end of an internal space formed by the at least one side wall and the rear wall;
   an illumination source illuminating the internal space and arranged at or adjacent the distal end;
   a first optical element coupled to the at least one side wall and spaced apart proximally from the illumination source to define a first light chamber within the internal space; and
   a second optical element coupled to the at least one side wall, parallel to the rear wall, and spaced apart proximally from the first optical element to define a second light chamber within the internal space,
   wherein a portion of the at least one side wall forming an internal surface of the second light chamber is non-reflective.

2. The pixel light source apparatus of claim 1, wherein the second optical element is optically transmissive, wherein the second optical element has a first surface on a first side facing the second light chamber and has a second surface opposite the first surface and forming a proximal end, and wherein the second optical element further comprises an anti-reflective coating on the second surface.

3. The pixel light source apparatus of claim 1, wherein the second optical element is optically transmissive, wherein the second optical element has a first surface on a first side facing the second light chamber and has a second surface opposite the first surface and forming a proximal end, and wherein the second optical element further comprises a first anti-reflective coating on the first surface and a second anti-reflective coating on the second surface.

4. The pixel light source apparatus of claim 1, wherein the illumination source comprises one or more light emitting diodes.

5. The pixel light source apparatus of claim 4, wherein the one or more light emitting diodes further comprise:
   at least one first light emitting diode for emission of red light or for light emission in a first spectral range;
   at least one second light emitting diode for emission of green light or for light emission in a second spectral range;
   at least one third light emitting diode for emission of blue light or for light emission in a third spectral range; and
   at least one fourth light emitting diode for emission of white light or for light emission in a fourth spectral range.

6. The pixel light source apparatus of claim 1, wherein each of the first optical element and the second optical element is a translucent diffusing optical element.

7. The pixel light source apparatus of claim 1, further comprising:
   a reflective coating covering at least part of the rear wall and at least part of the at least one side wall within the first light chamber.

8. The pixel light source apparatus of claim 7, wherein the reflective coating is selected from the group consisting of: barium sulfate, a white paint, a silver paint, a white polymer, a reflective polymer, a nano-structured reflective composition, zinc sulfide, titanium dioxide, magnesium fluoride, silicon dioxide, and combinations thereof.

9. The pixel light source apparatus of claim 1, further comprising:
   a non-reflective coating covering at least part of the at least one side wall within the second light chamber.

10. The pixel light source apparatus of claim 9, wherein the non-reflective coating is selected from the group consisting of: a flat black paint, a flocking, carbon black, carbon nanotubes, a nano-structured light absorbing composition, and combinations thereof.

11. The pixel light source apparatus of claim 1, further comprising:
    a transparent or translucent lens or cover coupled to the illumination source.

12. The pixel light source apparatus of claim 1, further comprising:
    a third optical element coupled to the at least one side wall, the third optical element arranged between and spaced-apart from the illumination source and the first optical element.

13. The pixel light source apparatus of claim 1, wherein the at least one side wall further comprises:
    a plurality of side walls coupled to each other to form an elongated polygonal structure enclosing the first and second light chambers in a transverse dimension.

14. The pixel light source apparatus of claim 13, wherein the elongated polygonal structure, together with the rear wall and the second optical element, define a frustum selected from the group consisting of: a pyramidal frustum, a triangular frustum, a square frustum, a pentagonal frustum, a hexagonal frustum, a septagonal frustum, an octagonal frustum, a conical frustum, and combinations thereof.

15. The pixel light source apparatus of claim 1, wherein a plurality of pixel light source apparatuses are coupled to each other to form a partially-spherical dome or shell.

16. A pixel light source system for a stimulus source for visual pathway testing, the pixel light source system comprising:
    a plurality of pixel light sources according to claim 1 coupled to each other to form a partially-spherical dome, each pixel light source arranged to emit light directed to a convergent location spaced apart from the partially-spherical dome; and
    a control and driver circuit coupled to the plurality of pixel light sources, the control and driver circuit adapted to implement a selected stimulus protocol to selectively energize each pixel light source of the plurality of pixel light sources.

17. The pixel light source system of claim 16, wherein the control and driver circuit comprises:
    a memory storing the selected stimulus protocol and a plurality of instructions;
    a plurality of switches, each switch coupled to a corresponding pixel light source of the plurality of pixel light sources;
    one or more current regulation circuits coupled to the plurality of switches; and a controller coupled to the plurality of switches and the one or more current regulation circuits, the controller adapted to generate a plurality of signals to the plurality of switches and the one or more current regulation circuits to selectively energize and de-energize each pixel light source of the plurality of pixel light sources according to the selected stimulus protocol and in response to the plurality of instructions.

18. The pixel light source system of claim 16, wherein the controller is further adapted to generate a plurality of signals to the plurality of switches and the one or more current regulation circuits to select a subset of the plurality of pixel light sources and to selectively energize and de-energize each pixel light source of the subset of the plurality of pixel light sources at a corresponding selected intensity, a corresponding selected spectral range, and a corresponding selected temporal frequency.

19. The pixel light source system of claim 16, wherein the selected stimulus protocol is an electroretinogram (ERG) protocol, or a Visual-Evoked Potential (VEP) protocol, or a Psychophysical Test protocol, selected from the group consisting of: a patterned stimulus protocol, a focal ERG or VEP stimulus protocol, a multi-focal ERG or VEP stimulus protocol, a pseudo-random pattern protocol, a chromatic focal ERG or VEP protocol, a pattern ERG or VEP protocol, a full-field (Ganzfeld) stimulus protocol, a flash ERG or VEP protocol, a paired-flash ERG or VEP protocol, a flicker ERG or VEP protocol, a scotopic threshold response (STR) protocol, a photopic negative response (PhNR) protocol, a step response protocol, an ON response protocol, an OFF response protocol, a chromatic response protocol, a visual field/perimetry protocol, a contrast sensitivity protocol, and combinations thereof.

20. The pixel light source system of claim 16, wherein, for each pixel light source:
the first optical element is a diffusing optical element; and
the second optical element is an optically transmissive optical element having a first surface on a first side facing the second light chamber and having a second surface opposite the first surface and forming a proximal end, the optically transmissive optical element further comprising a first, anti-reflective coating on the second surface.

21. The pixel light source system of claim 20, wherein, for each pixel light source, the illumination source comprises one or more light emitting diodes, the one or more light emitting diodes comprising:
at least one first light emitting diode for emission of red light or for light emission in a first spectral range;
at least one second light emitting diode for emission of green light or for light emission in a second spectral range;
at least one third light emitting diode for emission of blue light or for light emission in a third spectral range; and
at least one fourth light emitting diode for emission of white light or for light emission in a fourth spectral range.

22. The pixel light source system of claim 20, further comprising:
a second, reflective coating covering at least part of the rear wall and at least part of the at least one side wall within the first light chamber.

23. The pixel light source system of claim 20, further comprising:
a third, non-reflective coating covering at least part of the at least one side wall within the second light chamber.

24. The pixel light source system of claim 20, further comprising:
a third, diffusing optical element coupled to the at least one side wall, the third optical element arranged between and spaced-apart from the illumination source and the first optical element.

25. The pixel light source system of claim 20, wherein the at least one side wall further comprises:
a plurality of side walls coupled to each other to form an elongated polygonal structure enclosing the first and second light chambers in a transverse dimension, and
wherein the elongated polygonal structure, together with the rear wall and the second optical element, define a frustum selected from the group consisting of: a pyramidal frustum, a triangular frustum, a square frustum, a pentagonal frustum, a hexagonal frustum, a septagonal frustum, an octagonal frustum, a conical frustum, and combinations thereof.

26. The pixel light source system of claim 16, wherein the partially-spherical dome spans an angular range between about 120° to 240° measured from the convergent location.

27. The pixel light source system of claim 16, wherein each pixel light source of the plurality of pixel light sources subtends less than 10° of visual angle measured from the convergent location.

28. The pixel light source system of claim 16, further comprising:
an operator control panel coupled to the control and driver circuit for input of the selected stimulus protocol; and
a subject interface coupled to the control and driver circuit.

29. A method of using the pixel light source system of claim 16 with a subject, comprising: using the pixel light source system, generating light stimulation to any arbitrary or selected portion of the retina of an eye of the subject.

30. A method of using the pixel light source system of claim 16 with a subject, with one or more electrodes coupled to the subject or with the system further comprising a subject interface, the method comprising:
using a first plurality of pixel light sources, generating light stimulation to any arbitrary or selected portion of the retina of an eye of the subject;
receiving signals from the one or more electrodes or from the subject interface;
correlating the received signals with one or more locations of the first plurality of pixel light sources; and
identifying one or more regions of the visual system of the subject based on the correlation.

31. The method of using the pixel light source system of claim 30, further comprising:
selectively and sequentially generating light stimulation to a plurality of selected portions of the retina of the eye of the subject; and
evaluating one or more functional changes where a local therapeutic intervention has been introduced.

32. The method of using the pixel light source system of claim 30, further comprising: diagnosing one or more identified regions of the visual system of the subject based on the correlation.

33. A pixel light source system for a stimulus source for visual pathway testing, the pixel light source system comprising:
a plurality of pixel light sources coupled to each other to form a partially-spherical dome, each pixel light source arranged to emit light directed to a convergent location of the partially-spherical dome, each pixel light source comprising:
a plurality of optically opaque side walls arranged to form a frustum structure;
a rear wall coupled to the plurality of optically opaque side walls, the rear wall forming a distal end of the frustum structure;

an illumination source arranged at or adjacent the distal end, the illumination source comprising one or more light emitting diodes;

a first, diffusing optical element coupled to the at least one side wall and spaced apart proximally from the illumination source to define a first light chamber;

a second, optically transmissive optical element coupled to the at least one side wall and spaced apart proximally from the first optical element to define a second light chamber, the second, optically transmissive optical element having a first surface on a first side facing the second light chamber and having a second surface opposite the first surface and forming a proximal end, the second, optically transmissive optical element further comprising a first, anti-reflective coating on the second surface;

a second, reflective coating covering at least part of the rear wall and at least part of the plurality of optically opaque side walls within the first light chamber; and a third, non-reflective coating covering at least part of the plurality of optically opaque side walls within the second light chamber; and a control and driver circuit coupled to the plurality of pixel light sources, the control and driver circuit adapted to implement a selected stimulus protocol to selectively energize each pixel light source of the plurality of pixel light sources.

* * * * *